US007173139B2

(12) United States Patent
MacMillan et al.

(10) Patent No.: US 7,173,139 B2
(45) Date of Patent: Feb. 6, 2007

(54) ENANTIOSELECTIVE 1,4-ADDITION OF AROMATIC NUCLEOPHILES TO α,β-UNSATURATED ALDEHYDES USING CHIRAL ORGANIC CATALYSTS

(75) Inventors: David W. C. MacMillan, Pasadena, CA (US); Nick A. Paras, Burbank, CA (US)

(73) Assignee: California Institute of Technology, Pasadena, CA (US)

( * ) Notice: Subject to any disclaimer, the term of this patent is extended or adjusted under 35 U.S.C. 154(b) by 574 days.

(21) Appl. No.: 10/394,758

(22) Filed: Mar. 21, 2003

(65) Prior Publication Data

US 2003/0236438 A1 Dec. 25, 2003

Related U.S. Application Data

(63) Continuation-in-part of application No. 10/187,635, filed on Jul. 1, 2002, now Pat. No. 6,784,323.

(60) Provisional application No. 60/338,451, filed on Dec. 5, 2001, provisional application No. 60/388,172, filed on Dec. 5, 2001, provisional application No. 60/301,875, filed on Jun. 29, 2001.

(51) Int. Cl.
*C07D 233/00* (2006.01)
*C07C 45/00* (2006.01)

(52) U.S. Cl. .................... 548/316.4; 568/459; 568/467

(58) Field of Classification Search ............ 548/316.4; 568/459, 467

See application file for complete search history.

(56) References Cited

U.S. PATENT DOCUMENTS

| | | | | |
|---|---|---|---|---|
| 4,324,884 | A | 4/1982 | White et al. | |
| 4,355,184 | A | 10/1982 | Kaku et al. | |
| 5,428,174 | A | 6/1995 | Reissenweber et al. | |
| 5,430,194 | A | 7/1995 | Barner et al. | |
| 5,786,373 | A | 7/1998 | Hartman et al. | |
| 5,977,290 | A | 11/1999 | Siebenhaar | |
| 6,040,262 | A | 3/2000 | Fougret et al. | |
| 6,307,057 | B1 * | 10/2001 | MacMillan et al. | 548/316.4 |
| 6,369,243 | B1 * | 4/2002 | MacMillan et al. | 549/459 |
| RE38,073 | E * | 4/2003 | Carpino | 530/333 |
| 6,784,323 | B2 * | 8/2004 | MacMillan | 568/459 |

FOREIGN PATENT DOCUMENTS

| | | |
|---|---|---|
| WO | WO 92/02505 | 2/1992 |
| WO | WO 03/047740 | 6/2003 |

OTHER PUBLICATIONS

Ahrendt et al. (2000), "New Strategies for Organic Catalysis: The First Highly Enantioselective Organocatalytic Diels—Alder Reaction," *J. Am. Chem. Soc.* 122(17):4243-4244.

Evans et al. (1997), "Chiral $C_2$-Symmetric Cu(II) Complexes as Catalysts for Enantioselective Intramolecular Diels-Alder Reactions. Asymmetric Synthesis of (-)-Isopulo'upone," *J. Org. Chem.* 62(4):786-787.

Frederickson (1997), "Opitcally Active Isoxazolidines *via* Asymmetric Cycloaddition Reactions of Nitrones with Alkenes: Applications in Organic Synthesis," *Tetrahedron* 53(2):403-425.

Ishihara et al. (1996), "A New Powerful and Practical BLA Catalyst for Highly Enantioselective Diels-Alder Reations: An Extreme Acceleration of Reaction Rate by Brønsted Acid," *J. Am. Chem. Soc.* 118(12):3049-3050.

Iwasawa et al. (1989), "Asymmetric Intramolecular Diels-Alder Reaction Catalyzed by the Chiral Titanium Reagent," *Chemistry Letters*, pp. 1947-1950.

Jen et al. (2000), "New Strategies for Organic Catalysis: The First Enantioselective Organocatalytic 1,3-Dipolar Cycloaddition," *J. Am. Chem. Soc.* 122(40):9874-9875.

Jensen et al. (2001), "Catalytic Asymmetric Friedel-Crafts Alkylation of β,γ-Unsaturated α-Ketoesters: Enantioselective Addition of Aromatic C—H Bonds to Alkenes," *Angew. Chem. Int. Edit.* 40(1):160-163.

Johannsen (1999), "An Enantioselective Synthesis of Heteroaromatic N-Tosyl α-Amino Acids," *Chem. Commun.*, pp. 2233-2234.

Maruoka et al. (1994), "Virtually Complete Blocking of α,β-Unsaturated Aldehyde Carbonyls by Complexation with Aluminum Tris(2,6-diphenylphenoxide)," *J. Am. Chem. Soc.* 116(9):4131-4132.

Ohta et al. (1996), "Novel 5-Hydroxytryptamine (5-$HT_3$) Receptor Antagonists. III. Pharmacological Evaluations and Molecular Modeling Studies of Optically Active 4,5,6,7-Tetrahydro-1H-Benzimidazole Derivatives," *Chem. Pharm. Bull.* 44(9):1707-1716.

Paras et al. (2001), "New Strategies in Organic Catalysis: The First Enantioselective Organocatalytic Friedel-Crafts Alkylation," *J. Am. Chem. Soc.* 123(18):4370-4371.

Shi et al. (1995), "Synthesis of Axially Dissymmetric Chiral Ammonium Salts by Quaternization of Secondary Amines with (R)-(+)-2,2'-Bis(bromomethyl)-6,6'-dinitrobiphenyl and (R)-(+)-2,2'-Bis(bromomethyl)-1,1'-binaphthyl and an Examination of Their Abilities as Chiral Phase-Transfer Catalysts," *J. Chem. Research* (S), pp. 46-47 (*J. Chem. Research* (M), pp. 0401-0411).

(Continued)

*Primary Examiner*—Joseph K. McKane
*Assistant Examiner*—Susannah L. Chung
(74) *Attorney, Agent, or Firm*—Mintz, Levin, Cohn, Ferris, Glovsky and Popeo P.C.

(57) ABSTRACT

Nonmetallic, chiral organic catalysts are used to catalyze the 1,4-addition of an aromatic nucleophile to an α,β-unsaturated aldehyde. The aromatic nucleophile may be an N,N-disubstituted aniline compound, or an analog thereof. The reaction is efficient and enantioselective, and proceeds with a variety of substituted and unsubstituted aromatic nucleophiles and aldehydes. The invention also provides a method for the deamination of aromatic N,N-disubstituted amines such as those resulting from the 1,4-addition of an aromatic nucleophile to an α,β-unsaturated aldehyde.

23 Claims, No Drawings

OTHER PUBLICATIONS

Solodin et al. (1990), "(5S)-5-Benzyl-2,2,3-trimethylimidazolidin-4-one as a Highly Effective Chiral Auxiliary for Asymmetric Reduction of α-Oxo Amides," *J. Chem. Soc., Chem. Commun.*, pp. 1321-1322.

Yang et al. (1998), "Design and Synthesis of Chiral Ketones for Catalytic Asymmetric Epoxidation of Unfunctionalized Olefins," *J. Am. Chem. Soc.* 120(24):5943-5952.

Northrup et al. (2002), "The First Direct and Enantioselective Cross-Aldol Reaction of Aldehydes," J. Am. Chem. Soc. Supporting Information, Northrup ja0262378, pp. S1-S7.

Schuster et al. (2000), "Catalysis of a Diels—Alder Reaction by Amidinium Ions," J. Org. Chem. 65:1697-1701.

Austin (2002), "Enantioselective Organocatalytic Indole Alkylations," *Journal of the American Chemical Society* 124(7):1172-1173.

Northrup et al. (2002), "The First General Enantioselective Catalytic Diels—AlderReaction with Simple α,β-Unsaturated Ketones," *J. Am. Chem. Soc.* 124(11):2458-2460.

* cited by examiner

ENANTIOSELECTIVE 1,4-ADDITION OF AROMATIC NUCLEOPHILES TO α,β-UNSATURATED ALDEHYDES USING CHIRAL ORGANIC CATALYSTS

CROSS-REFERENCE TO RELATED APPLICATIONS

This is a continuation-in-part of U.S. Ser. No. 10/187,635, filed Jul. 1, 2002, now U.S. Pat. No. 6,784,323 which claims priority under 35 U.S.C. §119(e)(1) to provisional U.S. Ser. No. 60/301,875, filed Jun. 29, 2001, Ser. No. 60/338,451, filed Dec. 5, 2001, and Ser. No. 60/338,172, filed Dec. 5, 2001. The disclosures of the aforementioned applications are incorporated by reference in their entireties.

TECHNICAL FIELD

This invention relates generally to catalysis of enantioselective reactions, and more particularly relates to enantioselective reactions involving the use of chiral organic compounds as catalysts in the addition of aromatic nucleophiles to α,β-unsaturated aldehydes.

BACKGROUND

Ancillary (or "spectator") ligand-metal coordination complexes (e.g., organometallic complexes) and compositions are useful as catalysts, stoichiometric reagents and therapeutic agents. The ancillary ligand contains functional groups that bind to one or more metal centers and remain associated therewith, providing an opportunity to modify the steric, electronic and chemical properties of the active sites of the complex, i.e., the metal centers.

Unfortunately, many organometallic reagents are expensive and depending on their catalytic activity may not be commercially viable. Moreover, many organometallic complexes are useful only for very specific chemical reactions and do not have broad utility as catalysts for a variety of different types of reactions. This problem may be emphasized for the catalysis of reactions leading to chiral molecules, particularly the conversion of either chiral or achiral molecules via enantioselective catalysis to provide a chiral product.

Over the last 30 years enantioselective catalysis has become one of the most important frontiers in exploratory organic synthetic research. In the pharmaceutical industry and other industries, the use of pure enantiomeric molecules is often important for safety and efficacy. Thus, in the production of pharmaceuticals, use of catalysts or reagents that preferentially produce one enantiomer of a molecule relative to another enantiomer is particularly advantageous. Unfortunately, the catalysts that produce such enantiomers are typically organometallic complexes that are specific for a particular reaction. In addition, there is no way to predict with any reasonable accuracy which enantiomer will result. Examples of organometallic catalysts used to prepare chiral materials include BINOL-based complexes (Mikami et al. (1994) *J. Am. Chem. Soc.* 116:2812; Kobayashi et al. (1994) *J. Am. Chem. Soc.* 116:4083; Mikami et al. (1989) *J. Am. Chem. Soc.* 111:1940; Mikami et al. (1994) *J. Am. Chem. Soc.* 116:4077; Keck et al. (1993) *J. Am. Chem. Soc.* 115:8467; Keck et al. (1995) *J. Am. Chem. Soc.* 117:2363), BINAP-based complexes (Miyashita et al. (1980) *J. Am. Chem. Soc.* 102:7932; Miyashita et al. (1984) *Tetrahedron* 40:1245; Takaya et al. (1986) *J. Org. Chem.* 51:629; Takaya et al. (1988) *Org. Synth.* 67:20; Cai et al. (1995) *Tetrahedron Lett.* 36:7991), DUPHOS complexes (Burk et al. (1990) *Organometallics* 9:2653; Burk et al. (1993) *J. Am. Chem. Soc.* 115:10125; Burk et al. (1992) *J. Am. Chem. Soc.* 114:6266; Burk et al. (1995) *J. Am. Chem. Soc.* 117:9375); salen-based complexes (i.e., organometallic complexes containing the N,N-bis(3,5-di-t-butylsalicylidene)-1,2-cyclohexane-diamino ligand; see, e.g., Li et al. (1993) *J. Am. Chem. Soc.* 115:5326, and Evans et al. (1993) *Tetrahedron Lett.* 34:7027), and bisoxazoline-containing compounds (Evans et al. (1993) *J. Am. Chem. Soc.* 1 15:6460; Evans et al. (1997) *J. Am. Chem. Soc.* 119:7893; Evans et al. (1996) *Tetrahedron Lett.* 37:7481; Corey et al. (1992) *Tetrahedron Lett.* 33:6807; Gothelfet al. (1996) *J. Org. Chem.* 61:346).

Despite the observed need and relatively few, narrow solutions, relatively few asymmetric transformations have been reported which employ organic molecules as reaction catalysts. There is tremendous potential for academic, economic and environmental benefit should versatile, chiral organic catalysts be developed. Only a few researchers have disclosed organic catalysts useful for preparing chiral materials. See, e.g., *Asymmetric Catalysis in Organic Synthesis*, Noyori, R., Ed. (New York: Wiley, 1994) and *Asymmetric Synthesis, Ojima*, I., Ed. (New York: VCH, 1993), and references cited therein. Also see Yang et al. (1998) *J. Am. Chem. Soc.* 120(24):5943–5952, who disclose the use of a dioxirane to catalyze enantioselective epoxidation, Shi et al. (1995) *J. Chem. Research* (*S*):46–47 (*J. Chem. Research* (*M*): 0401–0411), who disclose preparation of chiral quaternary ammonium salts stated to be useful as chiral phase-transfer catalysts by reaction of (R)-(+)-2,2-bis(bromomethyl)-6,6-dinitrobiphenyl and (R)-(+)-2,2-bis (bromomethyl)-1,1-binaphthyl with cyclic amines such as pyrrolidine, piperidine and 4-hydroxypiperidine. International Patent Publication No. WO 92/02505 to Castelijns also discloses use of a secondary amine in a catalytic transformation, i.e., in conversion of an unsaturated imine to a pyridine product, by reaction with an aldehyde or ketone.

Recently, however, certain organic catalysts have been disclosed as generally useful in a variety of enantioselective transformations, by lowering the LUMO (lowest unoccupied molecular orbital) of a reactant to facilitate reaction thereof. The organic catalysts are acid addition salts of nonmetallic compounds containing a Group 15 or Group 16 heteroatom, e.g., chiral amines, exemplified by the imidazolidinone salt (5S)-5-benzyl-2,2,3-trimethylimidazolidin-4-one hydrochloride (I)

(I)

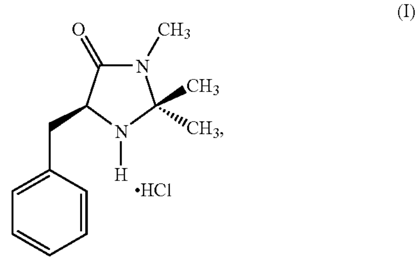

while exemplary reactants are α,β-unsaturated carbonyl compounds, including α,β-unsaturated aldehydes as well as α,β-unsaturated ketones. Such catalysts and reactions are described in U.S. Pat. No. 6,307,057 to MacMillan and U.S. Pat. No. 6,369,243 to MacMillan et al., which disclose the utility of (I) and other chiral amine salts in catalyzing a variety of reactions, including cycloaddition reactions, 1,4 nucleophile conjugate addition reactions, 1,4 radical addition reactions, organometallic insertion reactions, and ene reactions.

The use of catalyst (I) in the LUMO-lowering activation of α,β-unsaturated aldehydes, in particular, has been reported by Ahrendt et al. (2000) J. Am. Chem. Soc. 122:4243–4244, Jen et al. (2000) J. Am. Chem. Soc. 122: 9874–9875, and Paras et al. (2001) J. Am. Chem. Soc. 123:4370–4371. The reaction proceeds via the reversible formation of an iminium ion intermediate, which can be in one of two enantiomeric configurations. Using propenal as a reactant and (I) as the catalyst, the possible iminium ion intermediates A and B are formed (Equation 1):

Equation 1:

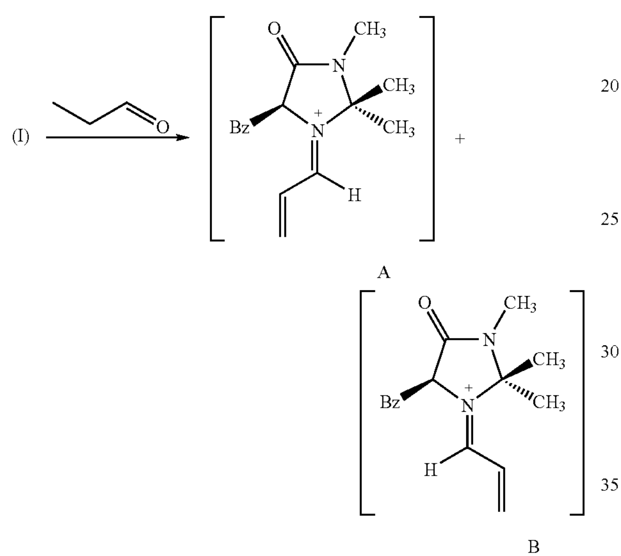

Upon further reaction, e.g., with cyclopentadiene in a Diels-Alder reaction, each intermediate results in a different enantiomeric product. That is, intermediate A gives rise to an exo product, while intermediate B results in the endo product (Equation 2):

Equation 2:

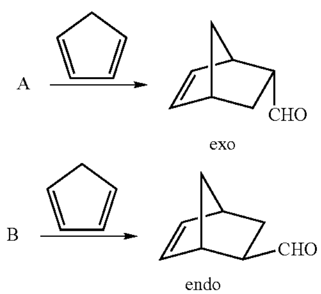

While imidazolidinone salt (I) and other chiral amines described in the foregoing references are quite valuable as enantioselective organic catalysts, there is a continuing need for nonmetallic catalysts that exhibit even higher levels of enantioselectivity across a diverse range of carbon-carbon bond forming reactions involving α,β-unsaturated carbonyl compounds as reactants. An ideal catalyst would be inexpensive and straightforward to synthesize, compatible with aerobic conditions, and provide for efficient reaction rates, good control over the geometry of the iminium ion intermediate, and high levels of enantiofacial discrimination.

Such catalysts have now been provided, as described in the parent application hereto, U.S. Ser. No. 10/187,635, filed Jul. 1, 2002, for "Enantioselective Transformation of α,β-Unsaturated Aldehydes Using Chiral Organic Catalysts" by David W. C. MacMillan, of common assignment herewith to the California Institute of Technology. The present invention is addressed to the use of the aforementioned catalysts in facilitating the enantioselective addition of aromatic nucleophiles to certain α,β-unsaturated carbonyl compounds, a reaction of paramount importance in the syntheses of natural products and analogs thereof.

SUMMARY OF THE INVENTION

The invention is addressed to the aforementioned need in the art, and, in one aspect, provides a method for carrying out an enantioselective nucleophilic addition reaction between an aromatic nucleophile and an α,β-unsaturated aldehyde. The reaction is carried out catalytically, using a nonmetallic, organic compound as the catalyst, thus avoiding the problems associated with traditional organometallic catalysts. The catalysts are readily synthesized from inexpensive, commercially available reagents, compatible with aerobic conditions, and provide the desired products in excellent yields with a high level of enantioselectivity. The chiral catalysts are imidazolidinone compounds having the structure of formula (IIA) or (IIB)

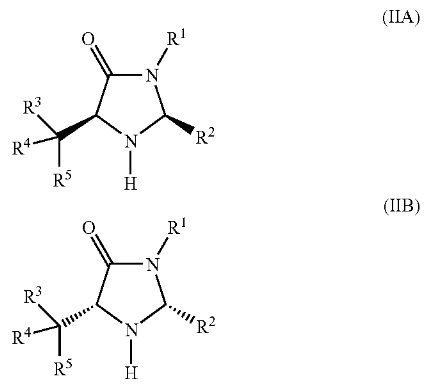

wherein:

$R^1$ is selected from $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl;

$R^2$ has the structure —$(L)_m$—$CR^6R^7R^8$ wherein m is zero or 1, L is $C_1$–$C_6$ alkylene, and $R^6$, $R^7$ and $R^8$ are $C_1$–$C_{12}$ hydrocarbyl;

$R^3$ and $R^4$ are independently selected from hydrogen, halo, hydroxyl, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl; and $R^5$ is a cyclic group optionally substituted with 1 to 4 non-hydrogen substituents and containing zero to 3 heteroatoms, and also include acid addition salts thereof.

In a related aspect, a process is provided for using imidazolidinone (IIA) or (IIB) to catalyze a nucleophilic addition reaction between an α,β-unsaturated aldehyde and an aromatic nucleophile by lowering the energy level of the lowest unoccupied molecular orbital (LUMO) of the aldehyde. The process involves contacting an α,β-unsaturated aldehyde with the aromatic nucleophile in the presence of (IIA) or (IIB), either in the form of an acid addition salt, or in the form of an electronically neutral compound combined with an acid.

The α,β-unsaturated aldehyde has the structure of formula (III)

(III)

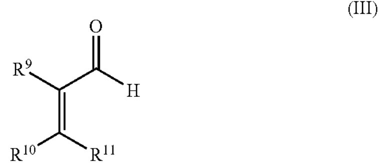

in which $R^9$, $R^{10}$ and $R^{11}$ are selected from hydrogen, $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, and functional groups, and at least one of $R^{10}$ and $R^{11}$ is generally, although not necessarily, hydrogen. The second reactant is an aromatic nucleophile that is capable of reacting with the α,β-unsaturated aldehyde by virtue of the lowered LUMO of the carbon-carbon double bond within the aldehyde in the presence of the imidazolidinone catalyst.

In a preferred embodiment, the aromatic nucleophile is of the formula (IV)

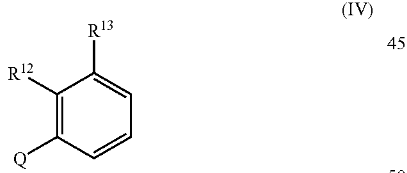

wherein Q is an electron-donating group, and $R^{12}$ and $R^{13}$ are independently selected from hydrogen, $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, and functional groups, or wherein $R^{12}$ and $R^{13}$, or $R^{12}$ and an atom within Q, taken together, form a cyclic structure selected from five-membered rings, six-membered rings, and fused five-membered and/or six-membered rings, wherein the cyclic structure is aromatic or alicyclic, substituted with zero to 4 non-hydrogen substituents and contains up to 3 heteroatoms per ring. The reaction with the aldehyde is a 1,4-addition reaction wherein the carbon atom para to Q adds to the β carbon of the aldehyde, which may be illustrated as follows:

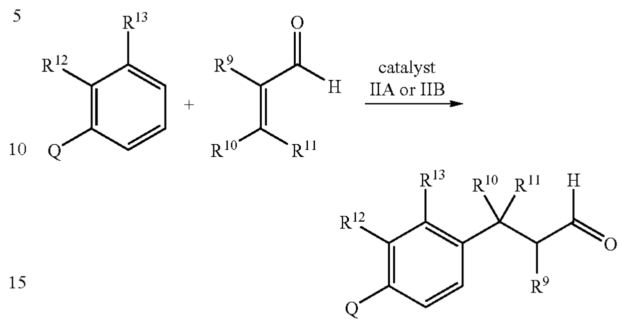

In another embodiment, a method is provided for the deamination of an N,N-disubstituted aromatic amine. The method is a one-pot reaction involving conversion of the amine to a quaternary ammonium salt, followed by reduction with sodium in liquid ammonia. The method does not require a metal catalyst, and provides the deaminated product in high yield. The aromatic tertiary amine may be the reaction product of a 1,4-addition reaction as described above, wherein the aromatic nucleophile is an N,N-disubstituted aniline compound, or contains an N,N-disubstituted aniline as a molecular segment. More generally, the amine may be represented by the formula Ar—$NR^{17}R^{18}$ wherein: Ar is aryl as defined herein, and may be substituted and/or heteroatom-containing, and may be monocyclic, bicyclic, or polycyclic; and $R^{17}$ and $R^{18}$, which may be the same or different, are nonhydrogen substituents, typically $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, or functional groups. The $R^{17}$ and $R^{18}$ substituents may also be linked to form a cyclic moiety, typically a five- or six-membered alicyclic structure that is optionally substituted and/or heteroatom-containing, and, if substituted, wherein any two substituents may be linked to form an additional cyclic structure.

DETAILED DESCRIPTION OF THE PREFERRED EMBODIMENTS

Unless otherwise indicated, the invention is not limited to specific molecular structures, substituents, synthetic methods, reaction conditions, or the like, as such may vary. It is also to be understood that the terminology used herein is for the purpose of describing particular embodiments only and is not intended to be limiting.

As used in the specification and the appended claims, the singular forms “a,” “an” and “the” include plural referents unless the context clearly dictates otherwise. Thus, for example, reference to “a catalyst” includes a single catalyst as well as a combination or mixture of two or more catalysts, reference to “a reactant” encompasses a combination or mixture of different reactants as well as a single reactant, and the like.

In this specification and in the claims that follow, reference will be made to a number of terms, which shall be defined to have the following meanings:

As used herein, the phrase “having the formula” or “having the structure” is not intended to be limiting and is used in the same way that the term “comprising” is commonly used. The term “independently selected from” is used herein to indicate that the recited elements, e.g., R groups or the like, can be identical or different.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. "Substituted alkyl" refers to alkyl substituted with one or more substituent groups, and the terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, preferably 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, preferably 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$–$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" as used herein, and unless otherwise specified, refers to an aromatic substituent generally containing 5 to 30 carbon atoms and containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 12 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms, while preferred aralkyl and alkaryl groups contain 6 to 20 carbon atoms, and particularly preferred such groups contain 6 to 12 carbon atoms.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$–$C_{24}$ alkoxy, $C_2$–$C_{24}$ alkenyloxy, $C_2$–$C_{24}$ alkynyloxy, $C_5$–$C_{20}$ aryloxy, acyl (including $C_2$–$C_{24}$ alkylcarbonyl (—CO-alkyl) and $C_6$–$C_{20}$ arylcarbonyl (—CO-aryl)), acyloxy (—O-acyl), $C_2$–$C_{24}$ alkoxycarbonyl (—(CO)—O-alkyl), $C_6$–$C_{20}$ aryloxycarbonyl (—(CO)—O-aryl), halocarbonyl (—CO)—X where X is halo), $C_2$–$C_{24}$ alkylcarbonato (—O—(CO)—O-alkyl), $C_6$–$C_{20}$ arylcarbonato (—O—(CO)—O-aryl), carboxy (—COOH), carboxylato ($—COO^-$), carbamoyl (—(CO)—$NH_2$), mono-substituted $C_1$–$C_{24}$ alkylcarbamoyl (—(CO)—NH($C_1$–$C_{24}$ alkyl)), di-substituted alkylcarbamoyl (—(CO)—N($C_1$–$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano ($—N^+{\equiv}C^-$), cyanato (—O—C≡N), isocyanato ($—O—N^+{\equiv}C^-$), isothiocyanato (—S—C≡N), azido ($—N{=}N^+{=}N^-$), formyl (—(CO)—H), thioformyl (—(CS)—H), amino (—$NH_2$), mono- and di-($C_1$–$C_{24}$ alkyl)-substituted amino, mono- and di-($C_5$–$C_{20}$ aryl)-substituted amino, $C_2$–$C_{24}$ alkylamido (—NH—(CO)-alkyl), $C_5$–$C_{20}$ arylamido (—NH—(CO)-aryl), imino (—CR═NH where R=hydrogen, $C_1$–$C_{24}$ alkyl, $C_5$–$C_{20}$ aryl, $C_6$–$C_{20}$ alkaryl, $C_6$–$C_{20}$ aralkyl, etc.), alkylimino (—CR═N(alkyl), where R=hydrogen, alkyl, aryl, alkaryl, etc.), arylimino (—CR═N(aryl), where R=hydrogen, alkyl, aryl, alkaryl, etc.), nitro (—$NO_2$), nitroso (—NO), sulfo (—$SO_2$—OH), sulfonato ($—SO_2—O^-$), $C_1$–$C_{24}$ alkylsulfanyl (—S-alkyl; also termed "alkylthio"), arylsulfanyl (—S-aryl; also termed "arylthio"), $C_1$–$C_{24}$ alkylsulfinyl (—(SO)-alkyl), $C_5$–$C_{20}$ arylsulfinyl (—(SO)-aryl), $C_1$–$C_{24}$ alkylsulfonyl (—$SO_2$-alkyl), $C_5$–$C_{20}$ arylsulfonyl (—$SO_2$-aryl), phosphono (—P(O)(OH)$_2$), phosphonato ($—P(O)(O^-)_2$), phosphinato ($—P(O)(O^-)$), phospho (—$PO_2$), and phosphino (—$PH_2$); and the hydrocarbyl moieties $C_1$–$C_{24}$ alkyl (preferably $C_1$–$C_{18}$ alkyl, more preferably $C_1$–$C_{12}$ alkyl, most preferably $C_1$–$C_6$ alkyl), $C_2$–$C_{24}$ alkenyl (preferably $C_2$–$C_{18}$ alkenyl, more preferably $C_2$–$C_{12}$ alkenyl, most preferably $C_2$–$C_6$ alkenyl), $C_2$–$C_{24}$ alkynyl (preferably $C_2$–$C_{18}$ alkynyl, more preferably $C_2$–$C_{12}$ alkynyl, most preferably $C_2$–$C_6$ alkynyl), $C_5$–$C_{30}$ aryl (preferably $C_5$–$C_{20}$ aryl, more preferably $C_5$–$C_{12}$ aryl), and $C_6$–$C_{30}$ aralkyl (preferably $C_6$–$C_{20}$ aralkyl, more preferably $C_6$–$C_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and aryl."

The terms "LUMO" and "HOMO" (abbreviations for lowest unoccupied molecular orbital and highest occupied molecular orbital, respectively) refer to the frontier orbitals of two reactants (such as an α,β-unsaturated carbonyl compound and a nucleophile), with the LUMO referring to the vacant orbital of lowest energy, in a first reactant (i.e., in an α,β-unsaturated aldehyde as described herein), and the HOMO referring to the orbital containing electrons of highest energy, in a second reactant.

The term "chiral" refers to a structure that does not have an improper rotation axis (Sn), i.e., it belongs to point group $C_n$ or $D_n$. Such molecules are thus chiral with respect to an axis, plane or center of asymmetry. Preferred "chiral" molecules herein are in enantiomerically pure form, such that a particular chiral molecule represents at least about 95 wt. % of the composition in which it is contained, more preferably at least about 99 wt. % of that composition.

The term "enantioselective" refers to a chemical reaction that preferentially results in one enantiomer relative to a second enantiomer, i.e., gives rise to a product of which a desired enantiomer represents at least about 50 wt. %. Preferably, in the enantioselective reactions herein, the desired enantiomer represents at least about 85 wt. % of the product, optimally at least about 95 wt. % of the product.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

Accordingly, the invention provides a method for carrying out an enantioselective nucleophilic addition reaction between an aromatic nucleophile and an α,β-unsaturated aldehyde using a nonmetallic organic compound as a catalyst. The catalysts are chiral imidazolidinone compounds having the structure of formula (IIA) or (IIB)

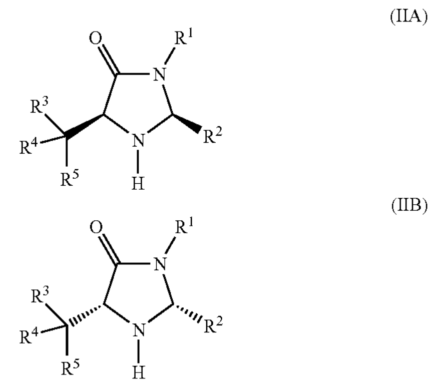

and may be in the form of an acid addition salt. In the reactions described herein, the catalyst used is either an acid addition salt of compound (IIA) or (IIB), or an acid is added to the reaction mixture to serve as a co-catalyst for compound (IIA) or (IIB) in electronically neutral form.

In formulae (IIA) and (IIB), the various substituents are as follows:

$R^1$ is selected from $C_1$–$C_{12}$ hydrocarbyl (e.g., alkyl, alkenyl, alkynyl, aryl, alkaryl, aralkyl, etc.), substituted $C_1$–$C_{12}$ hydrocarbyl (e.g., substituted alkyl, alkenyl, alkynyl, aryl, alkaryl, aralkyl, etc.), heteroatom-containing $C_1$–$C_{12}$ hydrocarbyl (e.g., heteroatom-containing alkyl, alkenyl, alkynyl, aryl, alkaryl, aralkyl, etc.), and substituted heteroatom-containing $C_1$–$C_{12}$ hydrocarbyl (e.g., substituted heteroatom-containing alkyl, alkenyl, alkynyl, aryl, alkaryl, aralkyl, etc.). Preferred $R^1$ substituents are $C_1$–$C_{12}$ hydrocarbyl such as $C_1$–$C_{12}$ alkyl, with $C_1$–$C_6$ alkyl groups (e.g., methyl) particularly preferred.

$R^2$ has the structure —$(L)_m$—$CR^6R^7R^8$ wherein m is zero or 1, L is $C_1$–$C_6$ alkylene, and $R^6$, $R^7$ and $R^8$ are $C_1$–$C_{12}$ hydrocarbyl. This is in contrast to imidazolidinone catalysts such as those described in Ahrendt et al. (2000) *J. Am. Chem. Soc.* 122:4243–4244, and Jen et al. (2000) *J. Am. Chem. Soc.* 122:9874–9875, in which the imidazolidinone is di-substituted at the 2-position with methyl groups. Here, the 2-position is substituted with a single group, $R^2$, relieving the steric obstruction immediately adjacent to the heterocycle in the catalysts of Ahrendt et al. and Jen et al. In a preferred embodiment, m is zero, $R^6$, $R^7$ and $R^8$ are $C_1$–$C_{12}$ alkyl. Optimally, $R^6$, $R^7$ and $R^8$ are $C_1$–$C_6$ alkyl, e.g., methyl (such that $R^2$ is then a tert-butyl group).

$R^3$ and $R^4$ are independently selected from hydrogen, halo, hydroxyl, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl. Preferably, $R^3$ and $R^4$ are hydrogen or $C_1$–$C_{12}$ hydrocarbyl, and, optimally, $R^3$ and $R^4$ are both hydrogen.

$R^5$ is a cyclic group optionally substituted with 1 to 4 non-hydrogen substituents and containing zero to 3 heteroatoms generally selected from N, O, and S. In a preferred embodiment, $R^5$ is monocyclic aryl or heteroaryl optionally substituted with 1 to 4 substituents selected from halo, hydroxyl, and $C_1$–$C_{12}$ hydrocarbyl. More preferably, $R^5$ is phenyl optionally substituted with 1 or 2 substituents selected from halo, hydroxyl, and $C_1$–$C_6$ alkyl, and in a particularly preferred embodiment, $R^5$ is an unsubstituted phenyl group.

The acid used to form the imidazolidinone salt or employed as a co-catalyst for the electronically neutral compound is generally a Brønsted acid. Suitable Brønsted acids are generally although not necessarily generally although not necessarily selected from acids having a pKa of less than about 5.

Combinations of Brønsted acids may also be used. Suitable acids include both organic and inorganic acids, with inorganic acids including, but not limited to, hydrochloric acid, hydrobromic acid, sulfuric acid, sulfurous acid, nitric acid, nitrous acid, perchloric acid, phosphoric acid, and chromic acid, and with organic acids exemplified by carboxylic acids, sulfonic acids, phosphonic acids, and aromatic alcohols, e.g., phenols, substituted with 1 to 5 electron-withdrawing substituents such as nitro, cyano, sulfonato, halo (i.e., Cl, F, Br or I) and halogenated alkyl (typically fluorinated alkyl, preferably perfluorinated lower alkyl such as trifluoromethyl). Particularly suitable organic acids are carboxylic acids and sulfonic acids having the structural formulas $R^x$—COOH and $R^x$—$SO_2$—OH wherein $R^x$ is aryl, alkyl, substituted aryl (e.g., halogenated aryl), or substituted alkyl (e.g., halogenated alkyl, particularly fluorinated and chlorinated alkyl). Preferred $R^x$ groups are methyl, halogenated methyl (e.g., fluorinated methyl such as trifluoromethyl, chlorinated methyl such as chloromethyl, dichloromethyl, and trichloromethyl, etc.), and nitrite-substituted methyl. Specific examples of preferred organic acids include acetic acid, propionic acid, glycolic acid, pyruvic acid, oxalic acid, malic acid, malonic acid, succinic acid, maleic acid, fumaric acid, tartaric acid, citric acid, benzoic acid, 2-nitrobenzoic acid, cinnamic acid, mandelic acid, methanesulfonic acid, ethanesulfonic acid, triflic acid, p-toluene sulfonic acid, salicylic acid, chloroacetic acid, dichloroacetic acid, trichloroacetic acid, trifluoroacetic acid, and combinations thereof. The Brønsted acid may or may not be chiral, and those Brønsted acids that are chiral may be used in isomerically pure form or as a racemic mixture.

Acid addition salts of the imidazolidinone may be synthesized by admixing the imidazolidinone (in uncharged, free base form) with a Brønsted acid HX, at a desired molar ratio, generally in the range of approximately 1:100 to 100:1, typically about 1:10 to 10:1, preferably about 1:2 to 2:1. Alternatively, the uncharged imidazolidinone may be combined with at least one salt $M^{q+}$ $q(X^-)$, thereby forming the desired imidazolidinone salt via ion exchange. A wide variety of salts may be used for this latter purpose, and the cation $M^{+q}$ can be virtually any cation, although q is generally 1, 2 or 3. Suitable M elements are typically chosen from Groups 2 to 13 of the Periodic Table of the Elements, but M may also be a polyatomic cation such as the ammonium ion $NH_4^+$. It should also be noted that the imidazolidinone salt can be prepared with two or more different Brønsted acids or metal salts, thereby forming a mixture of imidazolidinone salts, i.e., salts containing different anions $X^-$.

For purposes of exemplification, a detailed description of one method for synthesizing the imidazolidinone salt (2S, 5S)-5-benzyl-2-tert-butyl-3-methylimidazolidin-4-one hydrochloride ((5S)-5-benzyl-2,2,3-trimethylimidazolidin-4-one hydrochloride) is described in Example 1.

The α,β-unsaturated aldehyde has the structure of formula (III)

(III)

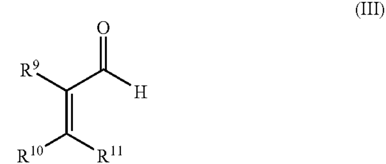

in which $R^9$, $R^{10}$ and $R^{11}$ are independently selected from hydrogen, $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, and functional groups. In a preferred embodiment, $R^9$, $R^{10}$ and $R^{11}$ are independently selected from hydrogen, $C_1$–$C_{24}$ alkyl, $C_2$–$C_{24}$ alkenyl, $C_2$–$C_{24}$ alkynyl, $C_1$–$C_{24}$ alkoxy, $C_2$–$C_{24}$ alkenyloxy, $C_2$–$C_{24}$ alkynyloxy, $C_5$–$C_{30}$ aryl, $C_5$–$C_{30}$ aryloxy, $C_5$–$C_{30}$ haloaryl, $C_5$–$C_{30}$ nitroaryl, $C_2$–$C_{24}$ alkoxyalkyl, $C_6$–$C_{30}$ aryloxyalkyl, hydroxyl, sulfhydryl, $C_2$–$C_{24}$ alkylcarbonyl, $C_6$–$C_{30}$ arylcarbonyl, $C_2$–$C_{24}$ alkoxycarbonyl, $C_6$–$C_{30}$ aryloxycarbonyl, halocarbonyl, $C_2$–$C_{24}$ alkylcarbonato, $C_6$–$C_{30}$ arylcarbonato, carboxy, carboxylato, carbamoyl, mono- and di-($C_1$–$C_{24}$ alkyl)-substituted carbamoyl, mono- and di-($C_5$–$C_{20}$ aryl)-substituted carbamoyl, amino, mono- and di-($C_1$–$C_{24}$ alkyl)-substituted amino, mono- and di-($C_5$–$C_{20}$ aryl)-substituted amino, $C_2$–$C_{24}$ alkylamido, $C_6$–$C_{30}$ arylamido, imino, $C_2$–$C_{24}$ alkylimino, $C_6$–$C_{30}$ arylimino, nitro, nitroso, sulfo, sulfonato, $C_1$–$C_{24}$ alkylsulfanyl, $C_5$–$C_{30}$ arylsulfanyl, $C_1$–$C_{24}$ alkylsulfinyl, $C_5$–$C_{30}$ arylsulfinyl, $C_1$–$C_{24}$ alkylsulfonyl, $C_5$–$C_{30}$arylsulfonyl, phosphono, phosphonato, phosphinato, phospho, phosphino, and combinations thereof. In addition, any two of $R^9$, $R^{10}$ and $R^{11}$ taken together can form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms.

In an exemplary embodiment, $R^9$ and $R^{11}$ are hydrogen, and $R^{10}$ is selected from hydrogen, $C_1$–$C_{12}$ alkyl, $C_1$–$C_{12}$ alkoxy, $C_5$–$C_{20}$ aryl, $C_2$–$C_{12}$ alkoxyalkyl, $C_2$–$C_{12}$ alkoxycarbonyl, $C_6$–$C_{20}$ aryloxycarbonyl, and $C_6$–$C_{20}$ aryloxyalkyl. Preferably, $R^{10}$ is selected from hydrogen, $C_1$–$C_6$ alkyl, $C_5$–$C_{12}$ aryl, $C_2$–$C_6$ alkoxycarbonyl, $C_6$–$C_{12}$ aryloxycarbonyl, and $C_6$–$C_{12}$ aryloxyalkyl, e.g., methyl, ethyl, benzoyloxy, halophenyl, nitrophenyl, etc.

The aromatic nucleophile, i.e., the aromatic compound that undergoes alkylation by virtue of the 1,4-addition reaction to an α,β-unsaturated aldehyde, may be any such compound that reacts with the α,β-unsaturated aldehyde by virtue of the lowered LUMO of the carbon-carbon double bond within the aldehyde in the presence of the imidazolidinone catalyst. In a preferred embodiment, the aromatic nucleophile has the structure of formula (IV)

(IV)

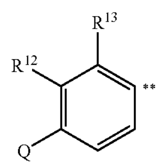

wherein ** indicates the carbon atom that will bind to the β carbon of the α,β-unsaturated aldehyde, and the substituents are as follows:

Q is an electron-donating group that increases the nucleophilicity of the aromatic ring. Electron-donating groups include, without limitation: $C_1$–$C_{24}$ alkyl, $C_1$–$C_{24}$ alkoxy, $C_5$–$C_{30}$ aryloxy, $C_6$–$C_{24}$ alkaryl, $C_1$–$C_{24}$ alkylthio, $C_2$–$C_{24}$ alkylcarbonyl, $C_6$–$C_{30}$ arylcarbonyl, $C_2$–$C_{24}$ alkylcarbonyoxyl, $C_6$–$C_{30}$ arylcarbonyloxy, and N,N-disubstituted amino —$NR^{14}R^{15}$, wherein $R^{14}$ and $R^{15}$ include, by way of example, $C_1$–$C_{30}$ hydrocarbyl, substituted $C_1$–$C_{30}$ hydrocarbyl, heteroatom-containing $C_1$–$C_{30}$ hydrocarbyl, substituted heteroatom-containing $C_1$–$C_{30}$ hydrocarbyl, and functional groups, or wherein $R^{14}$ and $R^{15}$ taken together form a cyclic structure selected from five-membered rings, six-membered rings, and fused five-membered and/or six-membered rings, wherein the cyclic structure is aromatic or alicyclic, is substituted with zero to 4 non-hydrogen substituents and may contain 1 to 3 additional heteroatoms (i.e., heteroatoms in addition to the nitrogen atom already present). More common electron-donating groups herein are $C_1$–$C_{12}$ alkyl, $C_1$–$C_{12}$ alkoxy, and —$NR^{14}R^{15}$, wherein $R^{14}$ and $R^{15}$ are selected from $C_1$–$C_{12}$ alkyl, $C_1$–$C_{12}$ heteroalkyl, substituted $C_1$–$C_{12}$ alkyl, substituted $C_1$–$C_{12}$ heteroalkyl, and $C_5$–$C_{12}$ aryl, or together form a five- or six-membered alicyclic group substituted with zero to 2 nonhydrogen substituents and may contain 1 or 2 additional heteroatoms. Particularly preferred $R^{14}$ and $R^{15}$ substituents are selected from $C_1$–$C_6$ alkyl and $C_5$ or $C_6$ aryl (e.g., phenyl), or are taken together to form a linkage resulting in a five- or six-membered alicyclic group, e.g., —$(CH_2)_4$— (forming a pyrrolidino ring) or —$(CH_2)_5$— (forming a piperidino ring). N,N-disubstituted amino groups are particularly preferred electron-donating groups herein, such that the aromatic nucleophile may be represented by the structure of formula (V)

(V)

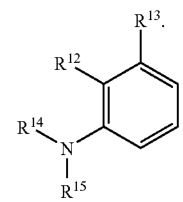

$R^{12}$ and $R^{13}$ are independently selected from hydrogen, $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, and functional groups. $R^{12}$ and $R^{13}$ can also be taken together to form $R^{12}$ and $R^{13}$ may also be taken together to form a cyclic structure selected from five-membered rings, six-membered rings, and fused five-membered and/or six-membered rings, wherein the cyclic structure is aromatic or alicyclic, substituted with zero to 4 non-hydrogen substituents and contains up to 3 heteroatoms per ring. Preferred $R^{12}$ and $R^{13}$ substituents include, without limitation, hydrogen, $C_1$–$C_{24}$ alkyl, $C_1$–$C_{24}$ alkoxy, $C_1$–$C_{24}$ alkylthio, $C_5$–$C_{30}$ aryl, $C_5$–$C_{30}$ aryloxy, $C_5$–$C_{30}$ arylthio, $C_2$–$C_{24}$ alkoxyalkyl, $C_6$–$C_{30}$ aryloxyalkyl, hydroxyl, and sulfhydryl, or wherein $R^{12}$ and $R^{13}$ taken together form a five- or six-membered aromatic ring optionally substituted and/or containing a heteroatom. Within the aforementioned group of preferred $R^{12}$ and $R^{13}$ substituents, particularly preferred substituents are selected from $C_1$–$C_6$ alkyl, $C_1$–$C_6$ alkoxy, and $C_1$–$C_6$ alkylthio, or wherein $R^{12}$ and $R^{13}$ taken together form an additional benzene ring. $R^{12}$ and $R^{13}$ may or may not be electron-donating substituents, insofar as the reaction with the aldehyde proceeds efficiently and at a high level of enantioselectivity even when $R^{12}$ or $R^{13}$ is an electron-withdrawing substituent such as a halogen atom (see Example 10).

In addition, $R^{14}$ may be linked to $R^{12}$ to form a cyclic structure, typically a five- or six-membered alicyclic ring that is optionally substituted and/or heteroatom-containing, i.e., contains heteroatoms in addition to the nitrogen atom indicated in the structure, preferably a five- or six-membered alicyclic group substituted with zero to 2 nonhydrogen substituents and optionally contains 1 or 2 additional heteroatoms. For example, $R^{14}$ and $R^{12}$ may form a bridge —$N(CH_3)$—$CH_2CH_2$— to give an N-methyl indoline core.

The product of the catalyzed 1,4-nucleophilic addition reaction of the invention is therefore an aldehyde substituted at the β carbon with the aromatic nucleophile as a substituent, with the point of attachment para to the electron-donating moiety Q:

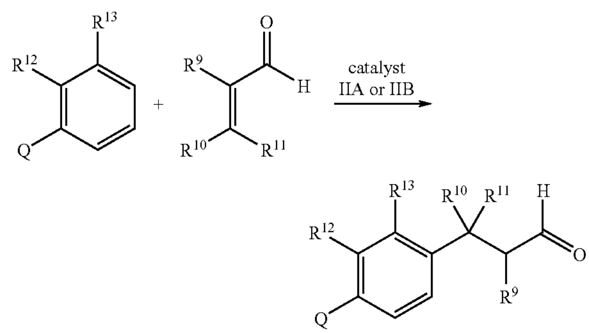

In the preferred embodiment, when $R^9$ and $R^{11}$ are hydrogen and Q is —$NR^{14}R^{15}$, it will be appreciated that the reaction is then as follows:

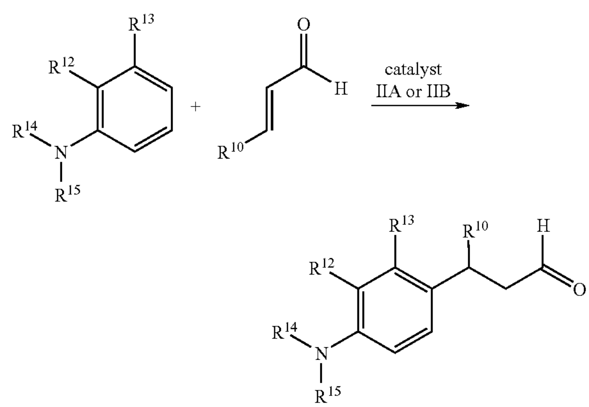

As documented in Examples 2–22, the 1,4-addition of an aromatic nucleophile to an α,β-unsaturated aldehyde in the presence of catalyst (IIA) proceeds in a synthetically straightforward manner with excellent levels of enantioselectivity.

Any of the reactions herein, including both preparation and use of the imidazolidinone salt, can be carried out on a solid support, using solid phase synthesis techniques. Solid-phase synthesis enables synthesis and use of the imidazolidinone salt in combinatorial chemistry processes, wherein an array or "matrix" of reactions are conducted in parallel on a single substrate. In such a case, the imidazolidinone itself (or the anion with which the cationic imidazolidinone is associated) can be bound either directly or indirectly to the surface of a solid substrate, if indirectly, through a cleavable or noncleavable linker. For example, the imidazolidinone can be linked to the surface of a substrate through any of $R^1$ through $R^5$. Any solid support may be used. Typical substrates are those conventionally used in solid phase chemistry and which allow for chemical synthesis thereon. The only limitation upon the materials useful for constructing substrates is that they must be compatible with the reaction conditions to which they are exposed. Suitable substrates useful in practicing the methods of the invention include, but are not limited to, organic and inorganic polymers (e.g., polyethylene, polypropylene, polystyrene, polytetrafluoroethylene), metal oxides (e.g., silica, alumina), mixed metal oxides, metal halides (e.g., magnesium chloride), minerals, quartz, zeolites, and the like. Other substrate materials will be apparent to those of skill in the art.

Process conditions: The catalytic reactions of the invention are preferably although not necessarily carried out in water, organic solvents or ionic liquids, i.e., in any solvent that allows retention and regeneration of the catalyst composition and removal of the reaction product following completion of the reaction. The reactions may be carried out in batch, semi-continuously or continuously, in air or an inert atmosphere, at autogenous pressure or higher, depending, for example, on the nature of the catalyst composition and reactants used. The reaction temperature will generally be in the range of about −100° C. to 100° C., preferably in the range of about −90° C. to 50° C. While lower temperatures, less than about 0° C., generally result in a higher yield and greater enantioselectivity, the reaction proceeds sufficiently rapidly for most purposes at ambient temperature, i.e., about 20° C. to 25° C.

The amount of catalyst (i.e., either an acid addition salt of the imidazolidinone, or a mixture of the imidazolidinone and an acid co-catalyst) is generally in the range of about 0.1 mole % to 1 stoichiometric equivalent, preferably in the range of about 1 mol % to 1 stoichiometric equivalent, and the molar ratio of the α,β-unsaturated aldehyde to the aromatic nucleophile is generally in the range of about 100:1 to 1:100, preferably in the range of about 10:1 to 1:10. Industrially, the reaction may be scaled up to 10,000 gallons or more. Catalysis may be heterogeneous or homogeneous. It will be appreciated by those skilled in the art of catalysis that the aforementioned process conditions may vary depending on the particular reaction, the desired product, the equipment used, and the like. Generally, the reaction product is obtained after completion of the reaction, wherein an optional extraction and/or catalyst recovery step and/or drying is followed by concentration or distillation to give the crude product and purification, e.g., by chromatography, sublimation, precipitation, extraction, crystallization with optional seeding and/or co-crystallization aids.

In another embodiment of the invention, a method is provided for deaminating the aldehyde resulting from the addition of an N,N-disubstituted analog of formula (V) to an α,β-unsaturated aldehyde of formula (III). The method involves quaternization of the amine moiety —$NR^{14}R^{15}$ with a suitable reagent, e.g., an alkyl halide $R^{16}$-Hal where $R^{16}$ is alkyl, preferably $C_1$–$C_6$ alkyl, and Hal is a halogen atom. An example of such a reagent is methyl iodide. The quaternary amine so formed, containing the substituent —$N(R^{14}R^{15}R^{16})^+$ (in association with the halide ion $Hal^-$), is then exposed to reductive conditions to provide the deaminated compound in which the original amine moiety is replaced with a hydrogen atom. The reaction is illustrated below:

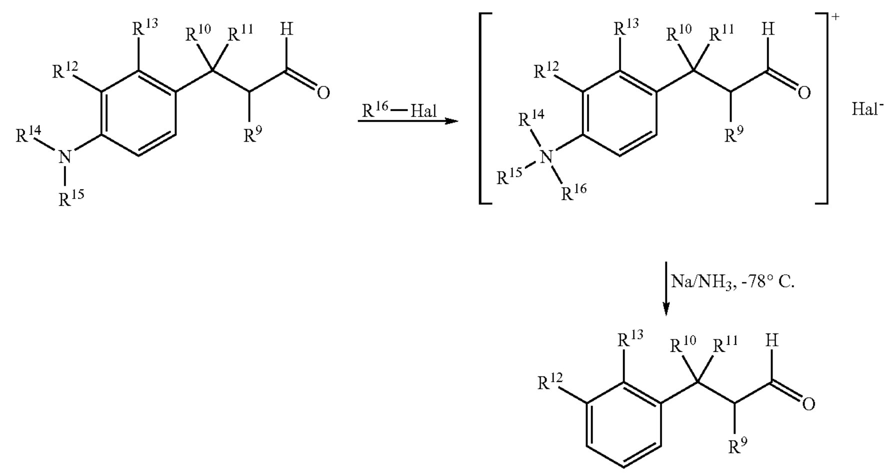

Advantageously, the reaction can be carried out as a “one-pot” synthesis, i.e., without need to isolate the quaternary amine intermediate. In the scheme, the deamination step is indicated as involving-reduction with sodium in liquid ammonia. Surprisingly, the yield obtained is extremely high, on the order of 90%, or even 95% or greater (see Example 24). It will be appreciated that other reducing agents and reduction systems can also be employed, although the $Na/NH_3$ system is particularly preferred. The ability to deaminate an aromatic amine in a one-pot method to give the desired product in high yield, without need for a metal-containing catalyst, is a significant accomplishment in the field of organic synthesis, insofar as aniline or an aniline analog may now be used as a benzene surrogate. By contrast, prior methods for deamination of aromatic amines involved either (a) a low yield reaction requiring conversion of the amine to a diazonium salt with nitrous acid, followed by admixture with an alcohol and heating; or (2) conversion of the amine to a diazonium salt followed by reduction with hypophosphorous acid in the presence of a metal catalyst, usually a copper (I) salt.

The aforementioned method extends to the deamination of N,N-disubstituted aromatic amines in general, i.e., extends to a reaction wherein an N, N-disubstituted aromatic amine is converted to a quaternary ammonium salt, followed by reduction with sodium in liquid ammonia. The amine is of the formula Ar—$NR^{17}R^{18}$ wherein: Ar is aryl as defined herein, and may be substituted and/or heteroatom-containing, and may be monocyclic, bicyclic, or polycyclic; and $R^{17}$ and $R^{18}$, which may be the same or different, are nonhydrogen substituents, typically $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, or functional groups. The $R^{17}$ and $R^{18}$ substituents may also be linked to form a cyclic moiety, typically a five- or six-membered alicyclic structure that is optionally substituted and/or heteroatom-containing, and, if substituted, wherein any two substituents may be linked to form an additional cyclic structure. Preferred $R^{17}$ and $R^{18}$ substituents are as defined elsewhere herein with respect to $R^{14}$ and $R^{15}$.

It is to be understood that while the invention has been described in conjunction with the preferred specific embodiments thereof, that the description above as well as the examples that follow are intended to illustrate and not limit the scope of the invention. Other aspects, advantages and modifications within the scope of the invention will be apparent to those skilled in the art to which the invention pertains.

All patents, patent applications, journal articles and other reference cited herein are incorporated by reference in their entireties.

Experimental:

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

Commercial reagents were purified prior to use following the guidelines of Perrin and Armarego, *Purification of Laboratory Chemicals*, Fourth Edition (Oxford, Butterworth-Heinemann, 1996). Organic solutions were concentrated under reduced pressure on a Büchi rotary evaporator. Methylene chloride was distilled from calcium hydride prior to use. Tetrahydrofuran was distilled from sodium benzophenone ketyl prior to use. Chloroform was distilled from calcium sulfate and potassium carbonate and passed through an alumina plug prior to use. Chromatographic purification of products was accomplished using forced-flow chromatography on ICN 60 32–64 mesh silica gel 63 according to the method of Still et al. (1978) *J. Org. Chem.* 43:2923. Thin-layer chromatography (TLC) was performed on EM Reagents 0.25 mm silica gel 60-F plates. Visualization of the developed chromatogram was performed by fluorescence quenching, anisaldehyde stain, potassium permanganate stain or dinitrophenylhydrazine stain.

$^1H$ and $^{13}C$ NMR spectra were recorded on Varian Mercury 300 spectrometers (300 MHz and 75 MHz respectively) as noted, and are internally referenced to residual protio solvent signals. Data for $^1H$ NMR are reported as follows: chemical shift (δ ppm), multiplicity (s=singlet, d=doublet, t=triplet, q=quartet, m=multiplet, br=broad), coupling constant (Hz), integration and assignment. Data for $^{13}C$ NMR are reported in terms of chemical shift (δ ppm). IR spectra were recorded on a Perkin Elmer Paragon 1000 spectrometer and are reported in terms of frequency of absorption ($cm^{-1}$). Mass spectra were obtained from the UC Irvine Mass Spectral facility. High performance liquid chromatography (HPLC) was performed on Hewlett-Packard 1100 Series chromatographs using Chiralpak AD column (0.46×25 cm) and AD guard (0.46×5 cm). Optical rotations were taken using a Jasco P-1010 polarimeter (WI lamp, 589 nm, 25° C.).

EXAMPLE 1

This example describes the synthesis of a catalyst used in the method of the invention in two steps from phenylalanine methyl ester, according to the following scheme:

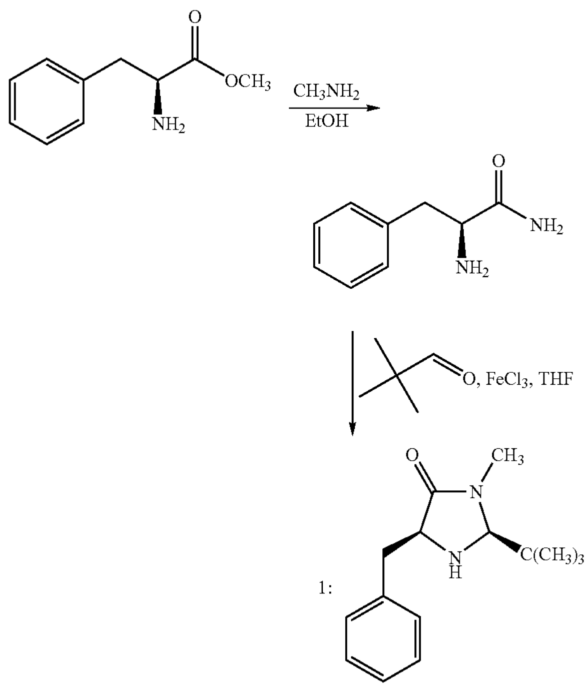

Hydrochloride salt of (2S,5S)-5-benzyl-2-tert-butyl-3-methyllimidazolidin-4-one (1): To a solution of ethanolic $MeNH_2$ (8.0 M, 50 ml) was added (S)-phenylalanine methyl ester (23.0 g, 130 mmol). The resulting solution was stirred at room temperature until the amino ester was judged to be consumed by TLC analysis. The resulting solution was then concentrated to provide (S)-phenylalanine N-methyl amide (18 g, 82% yield) as a white solid. To a flask containing (S)-phenylalanine N-methyl amide (8.9 g, 50 mmol) was added THF (100 ml), trimethylacetaldehyde (5.4 g, 50 mmol), $FeCl_3$ (1.7 g, 10 mmol) and 4Å MS (5.0 g). The resulting mixture was stirred at room temperature for 36 h, then washed with $H_2O$ (3×100 mL). The combined organics were concentrated and the resulting residue was treated with HCl (27 mL, 1N in ether). The resulting heterogeneous mixture was filtered to removed the undesired trans isomer. HCl salt and the resulting solution was concentrated. The residue was recrystallized (9:1 pentane/$CH_2Cl_2$) to provide the product (1) as a crystalline solid (2.88 g, 23% yield, >99% ee). IR (film) 3343, 2958, 1605, 1028 $cm^{-1}$; $^1H$ NMR (300 MHz, $CDCl_3$) δ7.31–7.17 (m, 5H, ArH), 4.04 (s, 1H, NCHN), 3.72–3.65 (m, 1H, $CHCH_2$), 3.13 (dd, J=4.1, 13.7 Hz, 1H, $CH_2$), 2.92 (dd, J=7.7, 13.7 Hz, 1H, $CH_2$), 2.90 (s, 3H, $NCH_3$), 0.82 (s, 9H, $C(CH_3)_3$); $^{13}C$ NMR (75 MHz, $CDCl_3$) δ175.3, 138.0, 129.8, 128.7, 126.8, 82.7, 77.8, 77.4, 76.9, 59.7, 38.6, 35.4, 31.0, 25.7; $[\alpha]_D$=−39.6 (c=1.0, $CHCl_3$). The enantiomeric ratio was determined by HPLC using a Chiralpak OD-H and OD guard column (3.0% i-PrOH/hexanes, 1 mL/min); (5S) isomer $t_r$=16.7 min, (5R) isomer $t_r$=20.1 min.

The trans (2R,5S) isomer of catalyst (1) can be converted to the desired cis (2S,5S) isomer as follows: A solution of trans-(2R,5S)-5-benzyl-2-tert-butyl-3-methylimidazolidin-4-one.HCl salt (6.0 g, 27.9 mmol) in $Et_2O$ (100 mL) was washed with saturated aqueous $NaHCO_3$ (100 mL) before the organics were separated and concentrated. To a flask containing the resulting residue was added THF (50 ml) and $FeCl_3$ (0.95 g, 5.6 mmol). The resulting solution was maintained at room temperature for 14 h, then washed with $H_2O$ (3×50 mL). The combined organics were concentrated and the resulting residue was treated with HCl (13 mL, 1N in ether). The resulting heterogeneous mixture was filtered to removed the undesired trans isomer.HCl salt and the resulting solution was concentrated. The residue was recrystallized (9:1 pentane/$CH_2Cl_2$) to provide the product as a crystalline solid (1.65 g, 22% yield, >99% ee).

It will be appreciated that the foregoing method can be readily adapted for the synthesis of analogous catalysts, i.e., imidazolidinones encompassed by formulae (IIA) and (IIB), by using appropriately substituted reactants as starting materials.

Examples 2–12 describe the use of (1) as a catalyst for a variety of reactions involving the 1,4-addition of an N,N-disubstituted aniline to an α,β-unsaturated aldehyde.

EXAMPLE 2

(R)-3-(4-Dimethylamino-2-methoxy-phenyl)-butyraldehyde (Table 1, entry 1). To a 2-dram vial equipped with a magnetic stir bar was added (2S,5S)-5-benzyl-2-tert-butyl-3-methylimidazolidin-4-one (12.3 mg, 0.050 mmol, 0.100 equiv), $CH_2Cl_2$ (0.50 ml), HCl (as a 4N solution in 1,4-dioxane, 12.5 μL, 0.050 mmol, 0.100 equiv), and N,N-dimethyl-m-anisidine (73.3 μL, 0.500 mmol, 1.00 equiv). The solution was cooled to −40° C. before crotonaldehyde (124 μL, 1.50 mmol, 3.00 equiv) was added. After 36 h, the reaction mixture was subjected directly to silica gel chromatography. Elution with 20% EtOAc in hexanes followed by concentration and removal of residual crotonaldehyde under vacuum afforded the product as a colorless oil in 86% yield (94.9 mg, 0.429 mmol); 89% ee. IR (film) 2958, 2874, 2834, 2719, 1721, 1615, 1568, 1516, 1462, 1441, 1352, 1238, 1133, 1034, 979.6, 814.0 $cm^{-1}$; $^1H$ NMR (300 MHz, $CDCl_3$) δ 9.67 (t, J=2.7 Hz, 1H, CHO), 7.03 (d, J=8.2 Hz, 1H, ArH), 6.31 (dd, J=2.5, 8.2 Hz, 1H, ArH), 6.27 (d, J=2.5 Hz, 1H, ArH), 3.83 (s, 3H, $OCH_3$), 3.63 (dq, J=7.1, 7.1 Hz, 1H, ArCH), 2.94 (s, 6H, $N(CH_3)_2$), 2.68 (ddd, J=2.5, 6.9, 15.9 Hz, $^1H$, $CH_2CO$), 2.55 (ddd, J=2.8, 7.7, 15.9 Hz, 1H, $CH_2CO$), 1.27 (d, 3H, $CHCH_3$); $^{13}C$ NMR (75 MHz, $CDCl_3$) δ 203.7, 157.8, 150.9, 127.5, 121.7, 15.1, 96.6, 55.4, 51.2, 41.0, 27.6, 20.9. HRMS (CI) exact mass calcd for ($C_{13}H_{19}NO_2$) requires m/z 222.1494 for [M+H]+, found m/z 222.1497. $[\delta]_D$=−9.5 (c=1.0, $CHCl_3$). The enantiomeric ratio of the product was determined by HPLC analysis of the corresponding alcohol (obtained by $NaBH_4$ reduction) using a Chiracel AD and AD guard column (3.0% ethanol/hexanes, 1 mL/min); S isomer $t_r$=21.6 min, R isomer $t_r$=23.1 min.

Determination of the absolute configuration (R)-3-(4-Dimethylamino-2-methoxyphenyl)-butyraldehyde by correlation to (S)-2-phenyl-butanol:

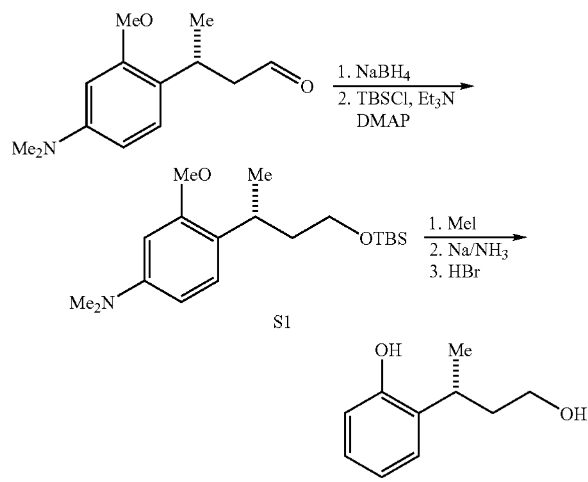

A solution of (R)-3-(4-dimethylamino-2-methoxy-phenyl)-butyraldehyde (520 mg, 2.35 mmol, 1.00 equiv) in $CH_2Cl_2$ (1.0 mL) was added to a stirring solution of sodium borohydride (86.9 mg, 2.35 mmol, 1.00equiv) in ethanol (5.0 mL). After 5 min, the reaction was diluted with saturated aqueous $NaHCO_3$ (30 mL) and $CH_2Cl_2$ (30 mL). The organic layer was separated and washed with saturated solutions of $NaHCO_3$ and NaCl. The resulting solution was then dried over $Na_2SO_4$ and concentrated in vacuo. The residual oil (525 mg, 2.35 mmol, 1.00 equiv) was exposed to tert-butyldimethylsilyl chloride (700 mg, 4.70 mmol, 2.00 equiv), triethylamine (0.70 mL, 5.0 mmol, 2.1 equiv), and DMAP (10 mg) in $CH_2Cl_2$ (3.0 mL). After 1 h, the reaction mixture was subjected directly to silica gel chromatography. Gradient elution with 2–20% EtOAc in hexanes followed by concentration in vacuo afforded S1 as a colorless oil in 72% yield (568 mg, 1.68 mmol), $[\alpha]_D$=−13.3 (c=1.12, $CHCl_3$). This oil was dissolved in $CH_3$ I (0.52 mL, 8.4 mmol, 5 equiv) and stirred for 10 h. The resulting mixture was then diluted with $Et_2O$ (20 mL), filtered and dried in vacuo to provide a white microcrystalline solid in 88% yield (706 mg, 1.47 mmol). The resulting ammonium salt (479 mg, 1.00 mmol, 1.00 equiv) was dissolved in freshly condensed liquid ammonia (20 ml) at −78° C. and treated with sodium (72 mg, 3.0 mmol, 3.0 equiv). After 3 min, the reaction mixture was quenched with excess methanol, diluted with ether (20 mL) and allowed to warm to ambient temperature. The ethereal solution was washed with aqueous HCl (1N) and saturated NaCl and subsequently dried over $Na_2SO_4$. The solvents were removed in vacuo and this oil was exposed to refluxing 48% HBr. After 8 h the reaction was partitioned between $Et_2O$ and water. The aqueous layer was extracted three times with EtOAc and the combined organics were washed with saturated $NaHCO_3$, dried over $Na_2SO_4$ and concentrated in vacuo. The residual oil was purified by silica gel chromatography (50% EtOAc in hexanes) to afford 6.40 mg (38 μmol, 3.8% yield from ammonium salt) of a colorless oil that was spectroscopically identical in all respects to the compound (S)-2-phenyl-butanol (Loiodice et. al. (1995), *Tet. Asymm.*, pp. 1001–1012). $[\alpha]_D$ (literature)=+16 (c=25, acetone); $[\alpha]_D$ (observed)=−6.1 (c=0.128, acetone), the opposite sign of the rotation indicating that we had produced the enantiomer of the known compound.

EXAMPLE 3

(R)-3-(4-Pyrolidin-1-yl-phenyl)-butyraldehyde (Table 1, entry 2): To a 2-dram vial equipped with a magnetic stir bar was added (2S,5S)-5-benzyl-2-tert-butyl-3-methylimidazolidin-4-one (49.3 mg, 0.200 mmol, 0.200 equiv) $CH_2Cl_2$ (0.33 ml), HCl (as a 4N solution in 1,4-dioxane, 50 μL, 0.200 mmol, 0.200 equiv), and 1-phenylpyrrolidine (144 μL, 1.00 mmol, 1.00 equiv). The solution was cooled to −20° C. before crotonaldehyde (166 μL, 2.00 mmol, 2.00 equiv) was added. After 48 h, the reaction mixture was subjected directly to silica gel chromatography. Elution with 20% EtOAc in hexanes followed by concentration in vacuo and removal of residual crotonaldehyde under high vacuum afforded the product as a pale yellow oil in 70% yield (147 mg, 0.676 mmol); 87% ee. IR (film) 2962, 2927, 2829, 2717, 1721, 1616, 1522, 1372, 814.0 $cm^{-1}$; $^1H$ NMR (300 MHz, $CDCl_3$) δ 9.71 (t, J=2.2 Hz, 1H, CHO), 7.10 (d, J=8.8 Hz, 2H, ArH), 6.54 (d, J=8.8 Hz, 2H, ArH), 3.32–3.21 (m, 5H, ArCH, $N(CH_2)_2$),2.71 (ddd, J=2.2, 7.1, 16.5 Hz, 1H, $CH_2CO$), 2.61 (ddd, J=2.2, 7.7, 16.0 Hz, 1H, $CH_2CO$), 2.03–1.96 (m, 4H, $CH_2(CH_2)_2CH_2$); $^{13}C$ NMR (75 MHz, $CDCl_3$) δ 202.7, 146.7, 132.0, 127.5, 111.8, 52.3, 47.8, 33.8, 25.7, 22.8. HRMS (CI) exact mass calcd for ($C_{14}H_{19}NO$) requires m/z 217.1467, found m/z 217.1467 $[\alpha]_D$=−33.9 (c=0.539, $CHCl_3$). The enantiomeric ratio of the product was determined by HPLC analysis of the corresponding alcohol (obtained by $NaBH_4$ reduction) using a Chiracel AD and AD guard column (6.0% ethanol/hexanes, 1 mL/min); R isomer $t_r$=20.9 min, S isomer $t_r$=24.4 min.

Determination of the absolute configuration (R)-3-(4-pyrrolidin-1-yl-phenyl)-butyraldehyde by correlation to (R)-3-(4-pyrrolidin-1-yl-phenyl)-butanol-tertbutyldimethylsilyl ether:

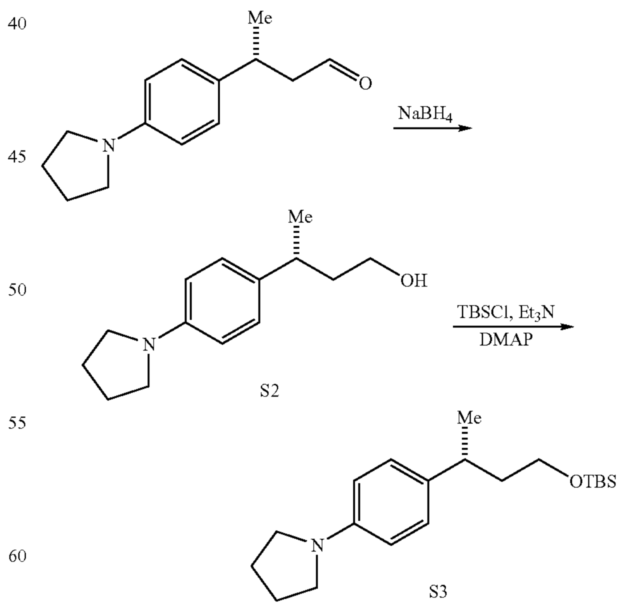

A solution (R)-3-(4-pyrolidin-1-yl-phenyl)-butyraldehyde (201 mg, 0.923 mmol, 1.00 equiv) in $CH_2Cl_2$ (0.5 mL) was added to a stirring solution of sodium borohydride (37.1 mg, 1.00 mmol, 1.08 equiv) in ethanol (3.0 mL). After 5 min, the reaction was diluted with saturated aqueous $NaHCO_3$ (50 mL) and $CH_2Cl_2$ (30 mL). The organic layer was separated and washed with saturated solutions of $NaHCO_3$ and NaCl. The resulting solution was then dried over $Na_2SO_4$ and concentrated in vacuo. The residual oil (201 mg, 0.915 mmol, 1.00 equiv) was exposed to tert-butyldimethylsilyl chloride (276 mg, 1.83 mmol, 2.00 equiv), triethylamine (0.28 mL, 2.0 mmol, 2.2 equiv), and DMAP (10 mg) in $CH_2Cl_2$ (1.5 mL). After one hour, the reaction mixture was subjected directly to silica gel chromatography. Elution with 10% $Et_2O$ in hexanes followed by concentration of two fractions in vacuo afforded 35 mg of S3 as a colorless oil (0.10 mmol, 11% yield) that was spectroscopically identical in all respects to (S)-4-benzoyloxy-3-(4-pyrolidin-1-yl-phenyl)-butyraldehyde. $[\alpha]_D$ (reference)=−28.7 (c=1.20, $CHCl_3$); $[\alpha]_D$ (observed)=−34.8 (c=0.994, $CHCl_3$).

EXAMPLE 4

(R)-3-(4-Dimethylamino-2-methoxy-phenyl)-pentanal (Table 1, entry 3): To a 2-dram vial equipped with a magnetic stir bar was added (2S,5S)-5-benzyl-2-tert-butyl-3-methylimidazolidin-4-one (24.6 mg, 0.100 mmol, 0.200 equiv), CH2Cl2 (0.50 ml), HCl (as a 4N solution in 1,4-dioxane, 25.0 μL, 0.100 mmol, 0.200 equiv), and N,N-dimethyl-m-anisidine (73.3 μL, 0.500 mmol, 1.00 equiv). The solution was cooled to −50° C. before pentenal (98.0 μL, 1.00 mmol, 2.00 equiv) was added. After 62 h, the reaction mixture was subjected directly to silica gel chromatography. Elution with 20% EtOAc in hexanes followed by concentration and removal of residual pentenal under vacuum afforded the product as a colorless oil in 68% yield (79.5 mg, 0.338 mmol); 88% ee. IR (film) 2959, 2926, 2871, 2839, 2800, 2721, 1718, 1616, 1569, 1517, 1351, 1237, 1136, 1034, 979.5, 812.9 cm-1;1H NMR (300 MHz, CDCl3) δ 9.63 (t, J=2.8 Hz, 1H, CHO), 6.97 (d, J=8.2 Hz, 1H, ArH), 6.30 (dd, J=2.5, 8.3 Hz, 1H, ArH), 6.26 (d, J=2.5 Hz, 1H, ArH), 3.81 (s, 3H, OCH3), 3.40 (dt, J=7.3, 7.4 Hz, 1H, ArCH), 2.94 (s, 6H, N(CH3)2), 2.66 (dd, J=2.7, 7.4 Hz, 2H, CH2CO), 1.72–1.61 (m, 2H, CH2CH3), 0.83 (t, J=7.4 Hz, 3H, CH2CH3); 13C NMR (75 MHz, CDCl3) 203.8, 158.2, 150.6, 128.4, 119.8, 105.0, 96.5, 55.5, 49.7, 1.1, 34.9, 28.4, 12.4. HRMS (CI) exact mass calcd for (C14H21NO2) requires m/z 236.1650 for [M+H]+, found m/z 236.1649. $[\alpha]_D$=−18.9 (c=0.970, CHCl3). The enantiomeric ratio of the product was determined by HPLC analysis of the corresponding alcohol (obtained by NaBH4 reduction) using a Chiracel AD and AD guard column (3.0% ethanol/hexanes, 1 mL/min); S isomer tr=11.5 min, R isomer tr=12.4 min.

Determination of the absolute configuration of (R)-3-(4-dimethylamino-2-methoxy-3 phenyl)-pentanal by correlation to (R)-3-ethyl-o-methoxy-dihydrocinnamic acid:

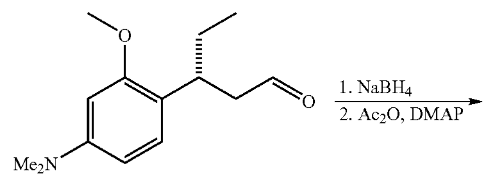

-continued

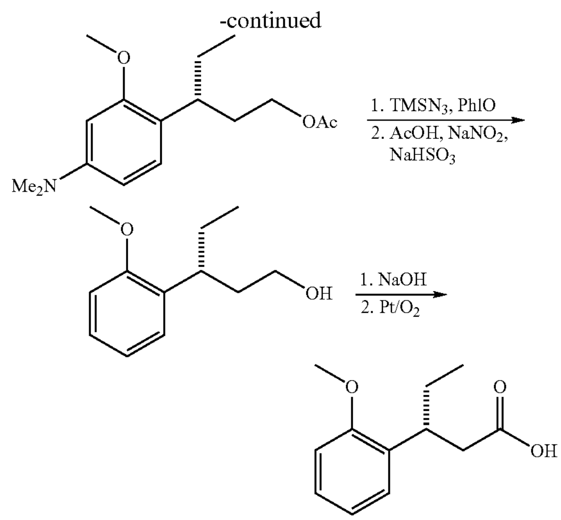

A solution of (R)-3-(4-dimethylamino-2-methoxy-phenyl)-pentanal (318 mg, 1.35 mmol, 1.00 equiv) in $CH_2Cl_2$ (1.0 mL) was added to a stirring solution of sodium borohydride (50.1 mg, 1.35 mmol, 1.00 equiv) in ethanol (5.0 mL). After 5 min, the reaction was diluted with saturated aqueous $NaHCO_3$ (30 mL) and $CH_2Cl_2$ (30 mL). The organic layer was then separated and washed with saturated solutions of $NaHCO_3$ and NaCl. The resulting solution was then dried over $Na_2SO_4$ and concentrated in vacuo. The residual oil was exposed to acetic anhydride (0.254 mL, 2.70 mmol, 2.00 equiv), triethylamine (0.42 mL, 3.0 mmol, 2.2 equiv), and DMAP (10 mg) in $CH_2Cl_2$ (5.0 mL). After one hour, the reaction mixture was subjected directly to silica gel chromatography. Elution with 25% EtOAc in hexanes followed by concentration in vacuo afforded 370 mg (1.32 mmol, 98% yield) of a colorless oil which was treated with iodosylbenzene (1.16 g, 5.28 mmol, 4.00 equiv) and trimethylsilylazide (0.74 ml, 5.6 mmol, 4.2 equiv) in $CH_2Cl_2$ (32 mL) at −40° C. according to the procedure of Jørgensen (Jørgensen et. al. (2000), *J. Am. Chem. Soc.* 122:12517). After 2 h, the reaction was warmed to room temperature and treated with THF and saturated aqueous $NaHCO_3$. The resulting mixture was stirred for 12 h then it was diluted with EtOAc, the organic phase was dried over $Na_2SO_4$ and concentrated in vacuo. This residue was dissolved in a mixture of ethanol/AcOH (50 mL: 7.5 mL) and treated with excess $NaNO_3$ (0.93 g in 15 mL $H_2O$) and $NaHSO_3$ (1.40 g in 15 mL $H_2O$). This mixture was extracted with $CHCl_3$ and the organic phase was washed with $H_2O$, dried over $Na_2SO_4$ and concentrated in vacuo. The resulting residue was dissolved in methanol (2.0 mL) and treated with an excess of NaOH (108 mg). After 15 min, the reaction mixture was diluted with $Et_2O$ (20 mL) and $H_2O$ (20 mL) then the organic layer was washed with saturated aqueous NaCl, dried over $Na_2SO_4$ and concentrated in vacuo. Silica gel chromatography of the residue (5–50% EtOAc in hexanes) afforded 41 mg of a colorless oil (0.21 mmol, 16% yield from dialkyl aniline). Finally, this material was taken up in EtOAc (3.4 mL) and added to a suspension of activated $PtO_2$ (150 mg, 0.060 mmol, 0.30 equiv) in $H_2O$/isopropanol (0.7 ml: 0.4 mL). This suspension was stirred under an $O_2$ atmosphere at 40° C. for 24 h. The reaction mixture was then filtered through Celite with additional EtOAc. The resulting solution was dried over $Na_2SO_4$ and concentrated in vacuo to afford 19.2 mg of a clear oil that was spectroscopically identical in all respects to the known compound (R)-3-ethyl-o-methoxy-dihydrocinnamic acid (Meyers et al. (1979), *J. Org. Chem.* 44:2250–2256) $[\alpha]_D$ (literature)=−21.3 (c=11.2, $CHCl_3$); $[\alpha]_D$ (observed)=−3.1 (c =1.0, $CHCl_3$).

EXAMPLE 5

(S)-4-Benzoyloxy-3-(4-dimethylamino-2-methoxy-phenyl)-butyraldehyde (Table 1, entry 4): To a 2-dram vial equipped with a magnetic stir bar was added (2S,5S)-5-benzyl-2-tertbutyl-3-methylimidazolidin-4-one (24.6 mg, 0.100 mmol, 0.100 equiv), N,N-dimethyl-anisidine hydrochloride (18.8 mg, 0.100 mmol., 0.100 equiv), $CHCl_3$ (1.00 ml), and N,N-dimethyl-m-anisidine (132 μL, 0.900 mmol, 0.900 equiv). The solution was cooled to −20° C. before 4-benzoyloxy-crotonaldehyde (0.380, 2.00 mmol, 2.00 equiv) was added as a solid. After 24 h, the reaction mixture was subjected directly to silica gel chromatography. Gradient elution with 10–25% EtOAc in hexanes followed by concentration and removal of residual pentenal under vacuum afforded the product as a colorless oil in 89% yield (304 mg, 0.889 mmol); 92% ee. IR (film) 2940, 2892, 2836, 2724, 1719, 1615, 1518, 1273, 1240, 1117, 712.5 $cm^{-1}$; $^1H$ NMR (300 MHz, $CDCl_3$) δ 9.74 (t, J=2.1 Hz, 1H, CHO), 8.01 (ddd, J=0.6, 1.1, 6.3 Hz., 2H, ArH), 7.58–7.40 (m, 3H, ArH), 7.08 (d, J=8.2 Hz, 1H, ArH), 6.30 (dd, J=2.5, 8.5 Hz, 1H, ArH), 6.25 (d, J=2.4 Hz, 1H, ArH), 4.51 (dd, J=5.5, 10.7 Hz, 1H, $CH_2O$), 4.42 (dd, J=8.2, 10.7 Hz, 1H, $CH_2O$), 4.08–3.98 (m, 1H, ArCH), 3.83 (s, 3H, $OCH_3$), 2.98–2.80 (m, 2H, $CH_2CO$), 2.95 (s, 6H, $N(CH_3)$; $^{13}C$ NMR (75 MHz, $CDCl_3$) 202.2, 166.6, 158.2, 151.3, 133.1, 130.3, 129.8, 129.0, 128.6, 115.6, 104.9, 96.3, 67.9, 55.4, 46.3, 50.0, 33.5. HRMS (CI) exact mass calcd for ($C_{20}H_{23}NO_4$) requires m/z 342.1705 for [M+H]+, found m/z 342.1705. $[\alpha]_D$ =−16.9 (c=0.751, $CHCl_3$). The enantiomeric ratio of the product was determined by HPLC analysis of the corresponding alcohol (obtained by $NaBH_4$ reduction) using a Chiracel AD and AD guard column (10% ethanol/hexanes, 1 mL/min); R isomer $t_r$=15.2 min, S isomer $t_r$=24.0 min.

Determination of the absolute configuration of (S)-4-benzoyloxy-3-(4-dimethylamino-2-methoxy-phenyl)-butyraldehyde by correlation to (R)-3-tert-butyldimethylsiloxy-2-(dimethylamino-2-methoxy-phenyl)-butanol:

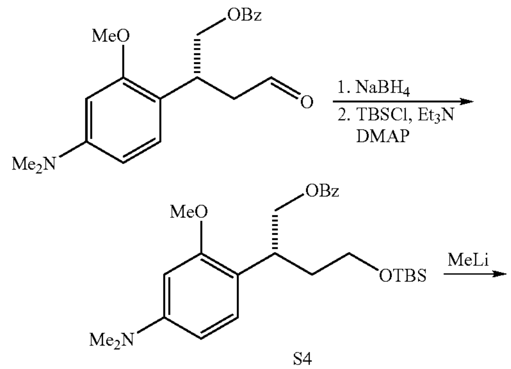

-continued

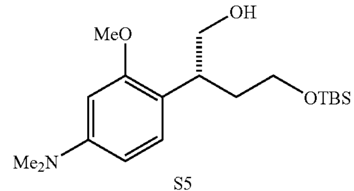

A solution (S)-4-benzoyloxy-3-(4- dimethylamino-2-methoxy-phenyl)-butyraldehyde (311 mg, 0.911 mmol, 1.00 equiv) in $CH_2Cl_2$ (0.5 mL) was added to a stirring solution of sodium borohydride (37.1 mg, 1.00 mmol, 1.10 equiv) in ethanol (3.0 mL). After 5 min, the reaction was diluted with saturated aqueous $NaHCO_3$ (30 mL) and $CH_2Cl_2$ (30 mL). The organic layer was then separated and washed with saturated solutions of $NaHCO_3$ and NaCl. The resulting solution was then dried over $Na_2SO_4$ and concentrated in vacuo. The residual oil (303 mg, 0.883 mmol, 1.00 equiv) was exposed to tert-butyldimethylsilyl chloride (266 mg, 1.77 mmol, 2.00 equiv), triethylamine (0.27 mL, 1.9 mmol, 2.2 equiv), and DMAP (10 mg) in $CH_2Cl_2$ (1.0 mL). After one hour, the reaction mixture was subjected directly to silica gel chromatography. Gradient elution with 10–25% $Et_2O$ in hexanes followed by concentration in vacuo afforded 400 mg of S4 as a colorless oil (0.874 mmol, 99% yield). To a solution of S4 (50 mg, 0.11 mmol, 1.0 equiv) in $Et_2O$ (0.55 mL) at 0° C. was added MeLi (1.6 M in hexanes, 0.21 mL, 0.33 mmol, 3.0 equiv). After 5 min, the reaction was treated with saturated aqueous $NH_4Cl$ (20 mL) and $Et_2O$ (20 mL). The organic phase was washed with saturated aqueous NaCl, dried over $Na_2SO_4$ and concentrated in vacuo. Silica gel chromatography of the resulting residue (50–100% $Et_2O$ in hexanes) afforded 25.4 mg (72.0 μmol, 65% yield) of S5 that was spectroscopically identical in all respects to S5 generated below from (R)-4-oxo-2-(4-dimethylamino-2-methoxyphenyl)-butyric acid methyl ester. $[\alpha]_D$ (reference)=−20.1 (c=1.00, $CHCl_3$); $[\alpha]_D$ (observed)=−21.6 (c=1.12, $CHCl_3$).

EXAMPLE 6

(S)-4-Benzoyloxy-3-(4-pyrolidin-1-yl-phenyl)-butyraldehyde (Table 1, entry 5): To a 2-dram vial equipped with a magnetic stir bar was added (2S,5S)-5-benzyl-2-tert-butyl-3-methylimidazolidin-4-one (6.13 mg, 0.025 mmol, 0.100 equiv) $CHCl_3$ (0.25 ml), HCl (as a 4N solution in 1,4-dioxane, 6.25 μL, 0.025 mmol, 0.100 equiv), 1-phenylpyrrolidine (36.1 μL, 0.025 mmol, 1.00 equiv). To the stirring solution at room temperature was added 4-benzoyloxycrotonaldehyde (95.0 mg, 0.5 mmol, 2.00 equiv). After 24 h, the reaction mixture was subjected directly to silica gel chromatography. Elution with 20–40% EtOAc in hexanes followed by concentration in vacuo afforded the product as a pale yellow oil in 73% yield (61.3 mg, 0.182 mmol); 90% ee. IR (film) 2961, 2888, 2825, 1717, 1715, 1616, 1522, 1487, 1450, 1374, 1271, 1176, 1115, 1069, 1026, 964.1, 812.7, 711.8 $cm^{-1}$; $^1H$ NMR (300 MHz, $CDCl_3$) δ 9.74 (t, J=1.9 Hz, 1H, CHO), 7.99 (d, J=7.1 Hz, 2H, ArH), 7.56 (t, J=7.7 Hz, 1H, ArH), 7.44 (t, J=7.7 Hz, 2H, ArH), 7.17 (d, J=8.8 Hz, 2H, ArH), 6.54 (d, J=8.8 Hz, 2H, ArH), 4.49 (dd, J=6.1, 11.0 Hz, 1H, $OCH_2$), 4.34 (dd, J=8.2, 10.4 Hz, 1H, $OCH_2$), 3.72–3.60 (m, 1H, ArCH), 3.30–3.21 (m, 4H, $N(CH_2)_2$), 2.94 (ddd, J=1.7, 6.6, 16.5 Hz, 1H, $CH_2CO$), 2.84 (ddd, J=2.2, 8.3, 17.1 Hz, 1H, $CH_2CO$), 2.03–1.95 (m, 4H, $CH_2(CH_2)_2CH_2$); $^{13}C$ NMR (75 MHz, $CDCl_3$) δ 201.5, 166.5, 147.3, 133.2, 130.2, 129.8, 128.6, 128.6, 126.1, 112.1, 69.0, 47.9, 47.2, 38.8, 25.8. HRMS (CI) exact mass calcd for ($C_{21}H_{23}NO_3$) requires n/z 338.1756, found m/z 338.1747. $[\alpha]_D$ =−5.1 (c=0.50, $CHCl_3$).

The enantiomeric ratio of the product was determined by HPLC analysis of the corresponding alcohol (obtained by $NaBH_4$ reduction) using a Chiracel AD and AD guard column (10% ethanol/hexanes, 1 mL/min); R isomer $t_r$=31.4 min, S isomer $t_r$=37.8 min.

Determination of the absolute configuration of (S)-4-benzoyloxy-3-(4-pyrolidin-1-ylphenyl)-butyraldehyde by correlation to (S)-2-(4-pyrolidin-1-yl-phenyl)-butan-1,4-diol:

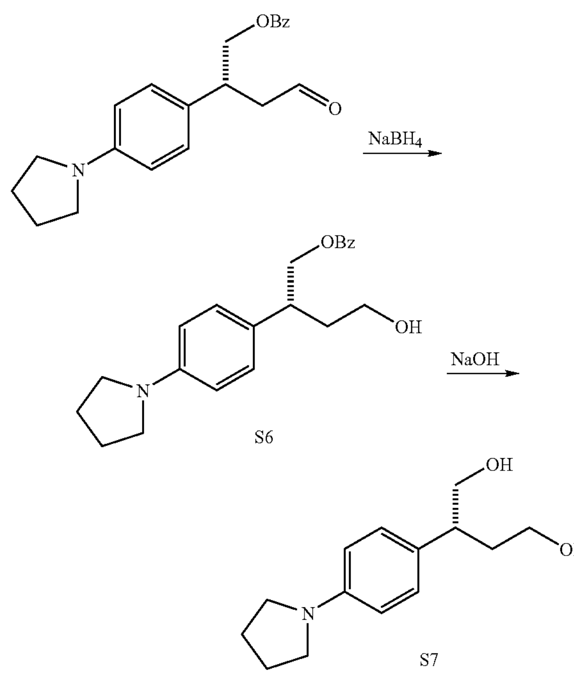

A solution of (S)-4-benzoyloxy-3-(4-pyrolidin-1-yl-phenyl)-butyraldehyde (508 mg, 1.51 mmol, 1.00 equiv) in $CH_2Cl_2$ (1.0 mL) was added to a stirring solution of sodium borohydride (55.9 mg, 1.51 mmol, 1.00 equiv) in ethanol (5.0 mL). After 5 min, the reaction was diluted with saturated aqueous $NaHCO_3$ (30 mL) and $CH_2Cl_2$ (30 mL). The organic layer was separated and washed with saturated solutions of $NaHCO_3$ and NaCl. The resulting solution was then dried over $Na_2SO_4$ and concentrated in vacuo to afford 464 mg (1.37 mmol, 91% yield) of a colorless oil. A portion of this substance (46.4 mg, 0.138 mmol, 1.00 equiv) was dissolved in methanol (2.0 mL) and treated with an excess of NaOH (100 mg, 2.50 mmol, 18.1 equiv). After one hour, the reaction mixture was partitioned between $CH_2Cl_2$ and $H_2O$, the organic layer was dried over $Na_2SO_4$ and concentrated in vacuo. The residue was subjected to silica gel chromatography (100% EtOAc) followed by concentration in vacuo to afford 24.6 mg of S7 as a white glassy solid (0.105 mmol, 76% yield) that was spectroscopically identical in all respects to S7 generated below from (R)-4-oxo-2-(4-pyrrolidin-1-yl-phenyl)-butyric acid methyl ester. $[\alpha]_D$ (reference)=−19.1 (c=1.03, $CHCl_3$); $[\alpha]_D$ (observed)=−15.9 (c=1.32, $CHCl_3$).

EXAMPLE 7

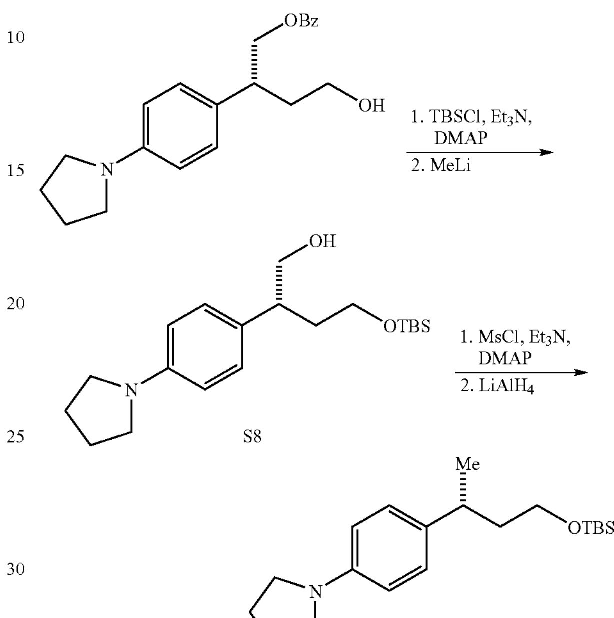

Conversion of (S)-4-benzoyloxy-3-(4-pyrolidin-1-yl-phenyl)-butyraldehyde to (R)-3-(4-Pyrolidin-1-yl-phenyl)-butanol-tert-butyldimethylsilyl ether: A solution of (S)-4-benzoyloxy-3-(4-pyrolidin-1-yl-phenyl)-butanol (464 mg, 1.37 mmol, 1.00 equiv) was exposed to tert-butyldimethylsilyl chloride (412 mg, 2.73 mmol, 2.00 equiv), triethylamine (0.42 mL, 3.0 mmol, 2.2 equiv), and DMAP (10 mg) in $CH_2Cl_2$ (1.5 mL). After one hour, the reaction mixture was subjected directly to silica gel chromatography. Elution with 10–25% $Et_2O$ in hexanes followed by concentration of two fractions in vacuo afforded 544 mg of a colorless oil (1.20 mmol, 87% yield). This compound was dissolved in $Et_2O$ (6.0 mL), cooled to 0° C. and treated with MeLi (1.6 M in hexanes, 3.75 mL, 6.0 mmol, 5.0 equiv). After 5 min, the reaction was treated with saturated aqueous NH4Cl (50 mL) and $Et_2O$ (50 mL). The organic phase was then washed with saturated aqueous NaCl, dried over $Na_2SO_4$ and concentrated in vacuo. Silica gel chromatography of the resulting residue (10–50% $Et_2O$ in hexanes) afforded 326 mg (0.932 mmol, 78% yield) of S8 as a colorless oil. A portion of this substance (0.193 mg, 0.551 mmol, 1.00 equiv) was treated with methanesulfonyl chloride (0.055 mL, 0.716 mmol, 1.30 equiv), triethylamine (0.12 mL, 0.83 mmol, 1.5 equiv), and DMAP (10 mg) in THF (10 mL). After 12 h, the resulting suspension was carefully added to a stirring suspension of lithium aluminum hydride (105 mg, 2.76 mmol, 5.0 equiv) in $Et_2O$ (10 mL). After 6 h, this mixture was diluted with saturated aqueous sodium potassium tartrate (50 mL) and $Et_2O$ (50 mL) and allowed to stir for an additional 8 h. The organic layer was separated, washed with saturated aqueous NaCl, dried over $Na_2SO_4$, and concentrated in vacuo. The resulting residue was purified via silica gel chromatography (10% $Et_2O$ in hexanes) to afford 12.0 mg of S3; $[\alpha]_D$=−28.7 (c=1.20, $CHCl_3$).

EXAMPLE 8

(R)-4-Oxo-2-(4-dimethylamino-2-methoxyphenyl)-butyric acid methyl ester (Table 1, entry 6): To an amber 2-dram vial equipped with a magnetic stir bar was added (2S,5S)-5-benzyl-2-tert-butyl-3-methylimidazolidin-4-one (6.13 mg, 0.0250 mmol, 0.100 equiv), $CHCl_3$ (0.25 ml), HCl (as a 4N solution in 1,4-dioxane, 6.25 μL, 0.0250 mmol, 0.100 equiv), and 3-dimethylamino-anisole (44 μL, 0.30 mmol, 1.2 equiv). The solution was cooled to −20° C. before oxobutenoic acid methyl ester (28.5 mg, 0.250 mmol, 1.00 equiv) was added. The resulting solution was maintained at −20° C. for 8 h and then subjected directly silica gel chromatography. Gradient elution with 20–40% EtOAc in hexanes afforded the product as a colorless oil in 73% yield (48.2 mg, 0.182 mmol); 91% ee. IR (film) 2950, 2903, 2838, 2727, 1730, 1616, 1569, 1519, 1462, 1440, 1356, 1242, 1171, 1114, 1033, 979.4, 814.6, 642.5 $cm^{-1}$; $^1H$ NMR (300 MHz, $CDCl_3$) δ 9.77 (t, J=1.1 Hz, 1H, CHO), 6.99 (d, J=8.2 Hz, 1H, ArH), 6.27 (dd, J=2.5, 8.5 Hz, 1H, ArH), 6.22 (d, J=2.5 Hz, 1H, ArH), 4.38 (dd, J=5.2, 9.1 Hz, 1H, ArCH), 3.81 (s, 3H, $ArOCH_3$), 3.66 (s, 3H, $CO_2CH_3$), 3.52 (ddd, J=1.4, 9.1, 18.1 Hz, 1H, $CH_2CO$), 2.94 (s, 6H, $N(CH_3)_2$), 2.67 (ddd, J=0.8, 4.9, 17.8 Hz, 1H, $CH_2CO$); $^{13}C$ NMR (75 MHz, $CDCl_3$) δ 201.0, 174.4, 157.5, 151.5, 129.3, 114.6, 104.9, 96.2, 55.6, 52.5, 46.7, 40.9, 39.2. HRMS (CI) exact mass calcd for ($C_{21}H_{23}NO_3$) requires m/z 266.1392 for [M+H]+, found m/z 266.1387. $[\alpha]_D$=−149.0 (c=1.0, $CHCl_3$). The enantiomeric ratio of the product was determined by HPLC analysis of the corresponding alcohol (obtained by $NaBH_4$ reduction in ethanol at 0° C.) using a Chiracel AD and AD guard column (6.0% ethanol/hexanes, 1 mL/min); S isomer $t_r$=26.0 min, R isomer $t_r$=27.8 min.

Determination of the absolute configuration (R)-4-oxo-2-(4-dimethylamino-2-methoxyphenyl)-butyric acid methyl ester by correlation to (R)-3-(4-dimethylamino-2-methoxyphenyl)-butanol tert-butyldimethylsilyl ether.

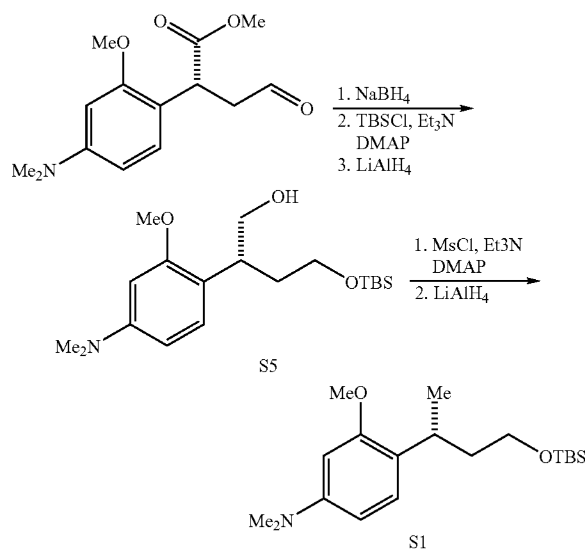

A solution of (R)-4-oxo-2-(4-dimethylamino-2-methoxyphenyl)-butyric acid methyl ester (288 mg, 1.30 mmol, 1.00 equiv) in $CH_2Cl_2$ (0.5 mL) was added to a stirring solution of sodium borohydride (48.3 mg, 1.30 mmol, 1.00 equiv) in ethanol (3.0 mL) at 0° C. After 5 min, the reaction was diluted with saturated aqueous $NaHCO_3$ (15 mL) and $CH_2Cl_2$ (15 mL). The organic layer was separated and washed with saturated solutions of $NaHCO_3$ and NaCl. The resulting solution was then dried over $Na_2SO_4$ and concentrated in vacuo. The residual oil was exposed to tert-butyldimethylsilyl chloride (392 mg, 2.60 mmol, 2.00 equiv), triethylamine (0.40 mL, 2.9 mmol, 2.2 equiv), and DMAP (10 mg) in $CH_2Cl_2$ (2.6 mL). After one hour, the reaction mixture was subjected directly to silica gel chromatography. Elution with 10–50% $Et_2O$ in hexanes followed by concentration in vacuo afforded 453 mg of a colorless oil (1.19 mmol, 91% yield from aldehyde). This compound was dissolved in $Et_2O$ (5.0 mL) and added to a suspension of lithium aluminum hydride (100 mg, 2.63 mmol, 2.21 equiv) in $Et_2O$ (10 mL) at 0° C. After 5 min, this mixture was diluted with saturated aqueous sodium potassium tartrate (50 mL) and $Et_2O$ (50 mL) and allowed to stir for an additional 8 h. The organic layer was separated, washed with saturated aqueous NaCl, dried over $Na_2SO_4$, and concentrated in vacuo. The resulting residue was purified via silica gel chromatography (20–100% EtOAc in hexanes) and concentrated in vacuo to afford 201 mg (0.568 mmol, 48% yield) of a pale yellow oil assigned as S5; $[\alpha]_D$=−20.1 (c=1.00, $CHCl_3$). This substance was treated with methanesulfonyl chloride (0.057 mL, 0.74 mmol, 1.30 equiv), triethylamine (0.12 mL, 0.85 mmol, 1.5 equiv), and DMAP (10 mg) in THF (8 mL). After 2 h, the resulting suspension was carefully added to a stirring suspension of lithium aluminum hydride (108 mg, 2.84 mmol, 5.0 equiv) in THF (10 mL). After 6 h, this mixture was diluted with saturated aqueous sodium potassium tartrate (50 mL) and $Et_2O$ (50 mL) and allowed to stir for an additional 3 h. The organic layer was separated, washed with saturated aqueous NaCl, dried over $Na_2SO_4$, and concentrated in vacuo. The resulting residue was purified via silica gel chromatography (25% EtOAc in hexanes) to afford 99.9 mg of S1 that was spectroscopically identical in all respects to S1 generated above from (R)-3-(4-dimethylamino-2- methoxy-phenyl)-butyraldehyde. $[\alpha]_D$ (reference)=−13.3 (c=1.12, $CHCl_3$); $[\alpha]_D$ (observed)=−11.6 (c=0.999, $CHCl_3$).

EXAMPLE 9

(S)-3-(4-pyrolidin-1-yl-2-methoxy-phenyl)-3-phenyl-propanol (Table 1, entry 7): To an amber 2-dram vial equipped with a magnetic stir bar was added (2S,5S)-5-benzyl-2-tert-butyl-3-methylimidazolidin-4-one hydrochloride (28.2 mg, 0.100 mmol, 0.200 equiv), $CH_2Cl_2$ (0.50 ml), and 1-(3-methoxy-phenyl)-pyrrolidine (83.6 μl, 0.500 mmol, 1.00 equiv). The solution was cooled to −50° C. before addition of cinnamaldehyde (167 μL, 1.00 mmol, 2.00 equiv). After 36 h, the reaction mixture was added drop-wise to a stirring suspension of $NaBH_4$ (41 mg) in ethanol (0.75 mL). After five min, the reduction was quenched with saturated aqueous $NaHCO_3$ solution and diluted with $CH_2Cl_2$. The layers were separated and the organic was washed with saturated aqueous $NaHCO_3$ and brine solutions. The resulting solution was dried over sodium sulfate and concentrated in vacuo and the residue was purified by silica gel chromatography. Gradient elution with 25–75% diethyl ether in hexanes afforded the product as a colorless oil in 82% yield (127.4 mg, 0.409 mmol); 84% ee. IR (film) 3356, 2941,2875, 2832, 1615, 1566, 1515, 1488, 1452, 1374, 1224, 1036, 699.6 $cm^{-}$; $^1H$ NMR (300

MHz, $CDCl_3$) δ 7.31–7.23 (m, 4H, ArH), 7.18–7.11 (m, 1H, ArH), 6.96 (d, J=8.8 Hz, 1H, ArH), 6.14 (dd, J=2.2, 8.2 Hz, 1H, ArH), 6.09 (d, J=2.2 Hz, 1H, ArH), 4.51 (dd, J=6.6, 9.3 Hz, 1H, ArCH), 3.83 (s, 3H, $OCH_3$), 3.70–3.48 (m, 2H, $CH_2OH$), 3.32–3.23 (m, 4H, $N(CH_2)_2$), 2.37–2.23 (m, 1H, $CHCH_2$), 2.22–2.10 (m, 1H, $CHCH_2$), 2.01–1.94 (m, 4H, $CH_2(CH_2)_2CH_2$), 1.89 (br s, 1H, OH); $^{13}C$ NMR (75 MHz, $CDCl_3$) δ 157.9, 147.8, 145.8, 129.0, 128.3, 128.2, 125.8, 119.9, 104.5, 95.3, 61.7, 55.9, 48.0, 36.6, 38.2, 25.8. HRMS (CI) exact mass calcd for ($C_{20}H_{25}NO_2$) requires m/z 311.1885, found m/Z 311.1880. $[\alpha]_D$=–60.5 (c=1.07, $CHCl_3$). The enantiomeric ratio of the product was determined by HPLC analysis using a Chiracel AD and AD guard column (10% ethanol/hexanes, 1 mL/min); S isomer $t_r$=15.1 min, R isomer $t_r$=28.6 min.

EXAMPLE 10

(S)-3-(4-Chloro-phenyl)-3-(4-pyrolidin-1-yl-2-methoxy-phenyl)-propanol (Table 1, entry 8): To an amber 2-dram vial equipped with a magnetic stir bar was added (2S,5S)-5-benzyl-2-tert-butyl-3-methylimidazolidin-4-one (24.6 mg, 0.100 mmol, 0.200 equiv), $CH_2Cl_2$ (0.50 ml), HCl (as a 4N solution in 1,4-dioxane, 25.0 µL, 0.100 mmol, 0.200 equiv) and 1-(3-methoxy-phenyl)-pyrrolidine (167 µl, 1.00 mmol, 2.00 equiv). The solution was cooled to −50° C. before addition of p-chloro-cinnamaldehyde as a solid (83.0 mg, 0.500 mmol, 1.00 equiv). After 80 h, the reaction mixture was added drop-wise to a stirring suspension of $NaBH_4$ (41 mg) in ethanol (0.75 mL). After five min, the reduction was quenched with saturated aqueous $NaHCO_3$ solution and diluted with $CH_2Cl_2$. The layers were separated and the organic was washed with saturated aqueous $NaHCO_3$ and brine solutions. The resulting solution was dried over sodium sulfate and concentrated in vacuo and the residue was purified by silica gel chromatography. Gradient elution with 25–75% diethyl ether in hexanes afforded the product as a colorless oil in 80% yield (137.8 mg, 0.399 mmol); 92% ee. IR (film) 3320, 2941, 2879, 2833, 1615, 1566, 1515, 1488, 1454, 1374, 1224, 1036, 1014, 808.8 $cm^{-1}$; $^1H$ NMR (300 MHz, $CDCl_3$) δ 7.20 (s, 4H, ArH), 6.93 (d, J=8.3 Hz, 1H, ArH), 6.13 (dd, J=2.1, 8.1 Hz, 1H, ArH), 6.07 (d, J=2.1 Hz, 1H, ArH), 4.45 (dd, J=6.6, 8.8 Hz, 1H, ArCH), 3.80 (s, 3H, $OCH_3$), 3.70–3.43 (m, 2H, $CH_2OH$), 3.32–3.20 (m, 4H, $N(CH_2)_2$), 2.32–2.03 (m, 2H, $CHCH_2$), 2.02–1.92 (m, 4H, $CH_2(CH_2)_2CH_2$), 1.74 (br s, 1H, OH); $^{13}C$ NMR (75 MHz, $CDCl_3$) δ 17.9, 147.9, 144.4, 131.4, 129.5, 128.9, 128.7, 128.4, 127.8, 119.2, 104.4, 95.3, 61.4, 55.8, 48.0, 38.2, 38.0, 25.8. HRMS (CI) exact mass calcd for ($C_{20}H_{24}ClNO_2$) requires m/z 345.1496, found m/z 345.1490. $[\alpha]_D$=–57.7 (c=1.90, $CHCl_3$). The enantiomeric ratio of the product was determined by HPLC analysis using a Chiracel AD and AD guard column (10% ethanol/hexanes, 1 mL/min); S isomer $t_r$=12.4 min, R isomer $t_r$=15.3 min.

EXAMPLE 11

(R)-3-(4-Nitro-phenyl)-3-(4-dimethylamino-2-methoxy-phenyl)-propionaldehyde (Table 1, entry 9): To a 2-dram vial equipped with a magnetic stir bar was added (2S,5S)-5-benzyl-2-tert-butyl-3-methylimidazolidin-4-one (24.6 mg, 0.100 mmol, 0.100 equiv), N,N-dimethyl -m-anisidine hydrochloride (18.8 mg, 0.100 mmol, 0.100 equiv), $CH_2Cl_2$ (1.00 ml), and N,N-dimethyl-m-anisidine (425 µL, 2.90 mmol, 2.90 equiv). The solution was cooled to −10° C. before p-nitro-cinnamaldehyde (177 mg, 1.00 mmol, 1.00 equiv) was added as a solid. After 48 h, the reaction mixture was subjected directly to silica gel chromatography. Gradient elution with 10–50% EtOAc in hexanes followed by concentration in vacuo afforded the product as a bright orange oil in 87% yield (285 mg, 0.867 mmol); 92% ee. IR (film) 2938, 2894, 2837, 2726, 1722, 1614, 1516, 1345, 1241, 1120, 1033, 980.1, 858.6, 814.9 $cm^{-1}$; $^1H$NMR (300 MHz, $CDCl_3$) δ 9.74 (t, J=1.9 Hz, 1H, CHO), 8.12 (td, J=2.2, 9.3 Hz, 2H, ArH), 7.42 (td, J=1.5, 9.3 Hz, 2H, ArH), 6.97 (d, J=8.3 Hz, 1H, ArH), 6.30 (dd, J=2.5, 8.8 Hz, 1H, ArH), 6.24 (d, J=2.2 Hz, 1H, ArH), 4.98 (t, J=7.8 Hz, 1H, ArCH), 3.79 (s, 3H, $OCH_3$), 3.21–3.09 (m, 2H, $CH_2CO$), 2.96 (s, 6H, $N(CH_3)_2$); $^{13}C$ NMR (75 MHz, $CDCl_3$) δ 201.2, 157.8, 152.3, 151.4, 146.5, 128.9, 128.6, 123.8, 118.0, 104.8, 96.4, 55.4, 48.4, 40.8, 38.2. HRMS (CI) exact mass calcd for ($C_{18}H_{20}N_2O_4$) requires m/z 328.1423, found m/z 328.1422. $[\alpha]_D$=0.58.1 (c=1.0, $CHCl_3$).

The enantiomeric ratio of the product was determined by HPLC analysis of the corresponding alcohol (obtained by $NaBH_4$ reduction of the aldehyde) using a Chiracel AD and AD guard column (10% ethanol/hexanes, 1 mL/min); R isomer $t_r$=25.6 min, S isomer $t_r$=29.5 min.

EXAMPLE 12

(S)-3-(4-Nitrophenyl)-3-(4-pyrolidin-1-yl-phenyl)-propionaldehyde (Table 1, entry 10): To an amber 2-dram vial equipped with a magnetic stir bar was added (2S,5S)-5-benzyl-2-tert-butyl-3-methylimidazolidin-4-one (24.6 mg, 0.100 mmol, 0.200 equiv) $CH_2Cl_2$ (0.50 ml), HCl (as a 4N solution in 1,4-dioxane, 25 µL, 0.200 mmol, 0.200 equiv), and p-nitrocinnemaldehyde (88.6 mg, 0.500 mmol, 1.00 equiv). The solution was cooled to −10° C. before addition of 1-phenylpyrrolidine (216 µL, 1.50 mmol, 3.00 equiv). After 48 h, the reaction mixture was subjected directly to silica gel chromatography. Gradient elution with 25–50% EtOAc in hexanes followed by concentration in vacuo afforded the product as a bright orange oil in 82% yield (133 mg, 0.411 mmol); 90% ee. IR (film) 2968, 2894, 2835, 2728, 1723, 1614, 1520, 1375, 1345, 1182, 1110, 859.2, 804.1 $cm^{-1}$; $^1H$ NMR (300 MHz, $CDCl_3$) δ 9.71 (t, J=1.4 Hz, 1H, CHO), 8.13 (d, J=8.8 Hz, 2H, ArH), 7.38 (d, J=8.8 Hz, 2H, ArH), 7.05 (d, J=8.8 Hz, 2H, ArH), 6.50 (d, J=8.8 Hz, 2H, ArH), 4.63 (t, J=7.7 Hz, 1H, ArCH), 3.29–3.09 (m, 6H, $CH_2CO$, $N(CH_2)_2$), 2.03–1.94 (m, 4H, $CH_2(CH_2)_2CH_2$); $^{13}C$ NMR (75 MHz, $CDCl_3$) δ 200.4, 152.2, 147.1, 128.6, 127.9, 124.1, 112.1, 49., 47.9, 44.2, 25.8. HRMS (CI) exact mass calcd for ($C_{19}H_{20}N_2O_3$) requires m/z 324.1474, found m/z 324.1474. $[\alpha]_D$=–3.75 (c=1.0, $CHCl_3$). The enantiomeric ratio of the product was determined by HPLC analysis of the corresponding acetate (obtained by $NaBH_4$ reduction of aldehyde and subsequent acylation with Ac2O) using a Chiracel AD and AD guard column (10% ethanol/hexanes, 1 mL/min); S isomer $t_r$=35.4 min, R isomer $t_r$=47.0 min.

The conditions, yield, and enantioselectivity for the reactions of Examples 2 through 12 are summarized in Table 1;

TABLE 1

Organocatalyzed Alkylation of Anilines 1a, 1b, and 1c with Representative αβ-Unsaturated Aldehydes 1a 1b 1c amine catalyst 1

10 mol % amine catalyst 1

$CH_2Cl_2$, 1.0M

| entry | aniline | $R^{10}$ | temp (° C.) | time (h) | % yield | % ee |
|---|---|---|---|---|---|---|
| 1 | 1a | Me | −40 | 36 | 86 | 89 |
| 2 | 1b | Me | −20 | 48 | 70 | 87 |
| 3 | 1a | Et | −50 | 48 | 68 | 88 |
| 4 | 1a | $CH_2OBz$ | −20 | 24 | 89 | 92 |
| 5 | 1b | $CH_2OBz$ | +20 | 24 | 73 | 90 |
| 6 | 1a | $CO_2Me$ | −20 | 8 | 90 | 92 |
| 7 | 1c | Ph | −50 | 36 | 82 | 84 |
| 8 | 1c | p-Cl—Ph | −50 | 80 | 80 | 92 |
| 9 | 1a | $p\text{-}NO^2$—Ph | −10 | 48 | 87 | 92 |
| 10 | 1b | $p\text{-}NO^2$—Ph | +20 | 48 | 82 | 90 |

As demonstrated by the data in Table 1, the (2S,5S)-5-benzyl-2-tert-butyl-imidazolidinone catalyst 1 (10 mol %, $CH_2Cl_2$) promoted the addition of N,N-dimethyl-3-anisidine (1a) and N-phenyl pyrrolidine (1b) to crotonaldehyde with high levels of enantioselectivity (entries 1 and 2, 70–86% yield, 87–89% ee). As also revealed in the table, variation in the steric contribution of the olefin substituent (X=Me, Et, $CH_2OBz$, entries 1–5) was possible without substantial loss in yield or enantiocontrol (68–89% yield, 87–92% ee). Similarly, the electronic nature of the α,β-unsaturated aldehyde component was not a limiting feature. For example, the reaction accommodated enals that do not readily participate in iminium formation (see entry 6, X=$CO_2Me$, 90% yield, 92% ee), as well as aldehydes that provide stable iminium intermediates (see entry 7, X=Ph, 82% yield, 84% ee).

Examples 13–22 describe the use of (1) to catalyze the 1,4-addition of differently substituted anilines to an α,β-unsaturated aldehyde.

EXAMPLE 13

(R)-4-Oxo-2-(4-dimethylamino-phenyl)-butyric acid methyl ester (Table 2, entries 1 & 2): To an amber 2-dram vial equipped with a magnetic stir bar was added (2S,5S)-5-benzyl-2-tert-butyl-3-methylimidazolidin-4-one (12.3 mg, 0.0500 mmol, 0.100 equiv), 4-oxobuteneoic acid methyl ester (57.1 mg, 0.500 mmol, 1.00 equiv), $CHCl_3$ (0.5 ml), HCl (as a 4N solution in 1,4-dioxane, 12.5 μL, 0.0500 mmol, 0.100 equiv), and N,N-dimethylaniline (76 μL, 0.60 mmol, 1.2 equiv). The solution was stirred for 5.5 h at ambient temperature and then subjected directly to silica gel chromatography. Gradient elution with 20–40% EtOAc in hexanes afforded the product as a colorless oil in 77% yield (90.0 mg, 0.383 mmol); 94% ee. The same reaction conducted at −10° C. was complete after 48 h and purified in identical fashion to give the product in 86% yield (101 mg, 0.429 mmol) and 96% ee. IR (film) 2950, 2902, 2844, 2809, 2728, 1732, 1614, 1523, 1437, 1353, 1230, 1166, 947.3, 818.8, 777.5 $cm^{-1}$; $^1H$ NMR (300 MHz, $CDCl_3$) δ 9.77 (s, 1H, CHO), 7.14 (d, J=7.1 Hz, 2H, ArH), 6.68 (d, J=7.6 Hz, 2H, ArH), 4.03 (dd, J=4.7, 9.9 Hz, 1H, ArCH), 3.66 (s, 3H, $OCH_3$), 3.35 (dd, J=9.9, 18.7 Hz, 1H, $CH_2CO$), 2.93 (s, 6H, $N(CH_3)_2$), 2.77 (dd, J=4.8, 18.3 Hz, 1H, $CH_2CO$); $^{13}C$ NMR (75 MHz, $CDCl_3$) δ 200.2, 174.0, 150.1, 128.5, 125.2, 112.9, 52.7, 47.8, 44.2, 40.8. HRMS (CI) exact mass calcd for ($C_{13}H_{17}NO_3$) requires m/z 236.1286, found m/z 236.1285. $[\alpha]_D$=−152.3 (c=1.0, $CHCl_3$). The enantiomeric ratio of the product was determined by HPLC analysis of the corresponding alcohol (obtained by $NaBH_4$ reduction) using a Chiracel AD and AD guard column (6.0% ethanol/hexanes, 1 mL/min); S isomer $t_r$=27.3 min, R isomer $t_r$=29.4 min.

Determination of the absolute configuration (R)-4-oxo-2-(4-dimethylamino-phenyl)-butyric acid methyl ester by correlation to (S)-2-phenyl-butan-1,4,-diol.

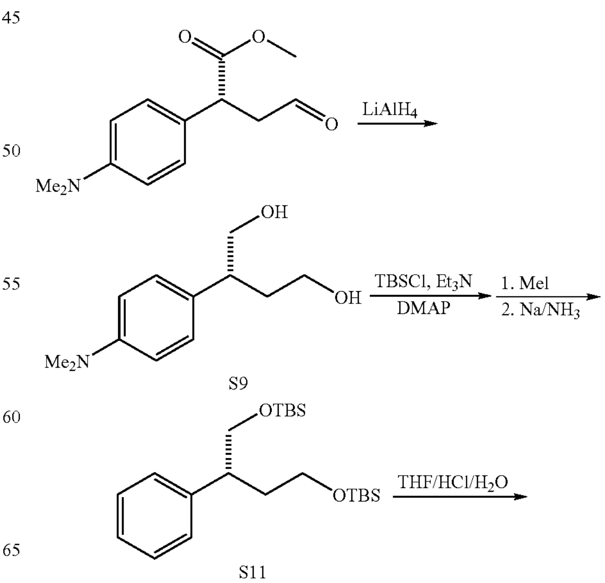

-continued

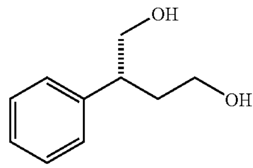

A solution of (R)-4- oxo-2-(4-dimethylamino-phenyl)-butyric acid methyl ester (1.78 g, 7.55 mmol, 1.00 equiv) in $CH_2Cl_2$ was added to a stirring suspension of lithium aluminum hydride (1.13 g, 29.8 mmol, 4.0 equiv) in $Et_2O$ (45 mL). After 5 min, this mixture was diluted with saturated aqueous sodium potassium tartrate (100 mL) and $Et_2O$ (100 mL) and allowed to stir for an additional 8 h. The organic layer was separated, washed with saturated aqueous NaCl, dried over $Na_2SO_4$, and concentrated in vacuo. The resulting residue was recrystallized from a hexanes, $Et_2O$ and DCM to give 0.630 g (3.01 mmol, 40% yield) of a white solid assigned as S9; $[\alpha]_D$=−23.1 (c=0.975, $CHCl_3$). This compound was then exposed to tert-butyldimethylsilyl chloride (907 mg, 6.02 mmol, 2.00 equiv), triethylamine (0.93 mL, 6.62 mmol, 2.2 equiv), and in $CH_2Cl_2$ (5.0 mL). After 5.5 h, the reaction mixture was subjected directly to silica gel chromatography. Gradient elution with 1–10% EtOAc in hexanes followed by concentration in vacuo afforded S10 as a faint-yellow oil in 49% yield (643 mg, 1.47 mmol); $[\alpha]_D$=−23.1 (c=0.975, $CHCl_3$). This oil was dissolved in $CH_3I$ (0.52 mL, 8.4 mmol, 5 equiv) and stirred for 10 h and subsequently concentrated in vacuo to provide a yellow microcrystalline solid in 97% yield (825 mg, 1.42 mmol). A portion of the ammonium salt (100 mg, 0.170 mmol, 1.00 equiv) was suspended in THF (20 mL) and added to a stirring solution of dissolved sodium (15.9 mg, 0.690 mmol, 4.00 equiv) in freshly condensed liquid ammonia (25 ml) at −78° C. After 30 min, the reaction mixture was quenched with excess methanol, diluted with ether (20 mL) and allowed to warm to ambient temperature. The ethereal solution was washed with aqueous HCl (1N) and saturated NaCl and subsequently dried over $Na_2SO_4$. This residue was purified by silica gel chromatography to afford 61.1 mg of S11 (0.155 mmol, 91% yield); $[\alpha]_D$=−28.7 (c=1.01, $CHCl_3$). This compound was treated with aqueous HCl (4N, 1.0 mL) and THF (1.0 mL) and stirred at ambient temperature for 16 h. Dilution of the reaction mixture with $CH_2Cl_2$ and saturated aqueous $NaHCO_3$ and subsequent separation, drying and concentration of the organic phase yielded a pale yellow oil. This compound was subjected to silica gel chromatography to afford 5.0 mg (30 μmol, 19% yield) of a substance that was spectroscopically identical in all respects to the known compound (S)-2-phenyl-butan-1,4,-diol.6 $[\alpha]_D$ (literature)=−13 (c=3.0, $CHCl_3$); $[\alpha]_D$ (observed)=−29.8 (c=0.50, $CHCl_3$).

EXAMPLE 14

(R)-4-Oxo-2-(4-dibenzylamino-phenyl)-butyric acid methyl ester (Table 2, entry 3): To an amber 2-dram vial under an argon atmosphere and equipped with a magnetic stir bar was added (2S,5S)-5-benzyl-2-tert-butyl-3-methylimidazolidin-4-one (12.3 mg, 0.0500 mmol, 0.100 equiv), 4-oxobuteneoic acid methyl ester (57.1 mg, 0.500 mmol, 1.00 equiv), $CHCl_3$ (0.5 ml), HCl (as a 4N solution in 1,4-dioxane, 12.5 μL, 0.0500 mmol, 0.100 equiv), and N,N-dibenzylaniline (273 mg, 1.00 mmol, 2.00 equiv). The solution was stirred for 24 h at ambient temperature and subjected directly to silica gel chromatography. Gradient elution with 20–40% EtOAc in hexanes afforded the product as a colorless oil in 65% yield (126 mg, 0.325 mmol); 96% ee. IR (film) 3028, 2949, 2904, 2844, 2725, 1729, 1717, 1613, 1520, 1434, 1451, 1360, 1231, 1166, 956.2, 816.0, 733.7, 696.5 $cm^{-1}$; $^1H$ NMR (300 MHz, $CDCl_3$) δ 9.76 (s, 1H, CHO), 7.22–7.36 (m, 10H, ArH), 7.05 (d, J=9.0 Hz, 2H, ArH), 6.68 (d, J=8.7 Hz, 2H, ArH), 4.64 (s, 4H, $ArCH_2$), 4.01 (dd, J=4.7, 9.9 Hz, 1H, ArCH), 3.66 (s, 3H, $OCH_3$), 3.33 (ddd, J=0.9, 9.9, 18.7 Hz, 1H, $CH_2CO$), 2.76 (ddd, J=0.8, 4.7, 18.4 Hz, 1H, $CH_2CO$); $^{13}C$ NMR (75 MHz, $CDCl_3$) δ 200.2, 173.9, 148.8, 135.5, 128.9, 128.7, 127.2, 126.8, 125.4, 112.8, 54.6, 52.7, 47.8, 44.1. HRMS (CI) exact mass calcd for ($C_{25}H_{25}NO_3$) requires m/z 387.1834, found m/z 387.1834. $[\alpha]_D$=−91.2 (c=1.0, $CHCl_3$).

The enantiomeric ratio of the product was determined by HPLC analysis of the corresponding alcohol (obtained by $NaBH_4$ reduction) using a Chiracel AD and AD guard column (6.0% ethanol/hexanes, 1 mL/min); S isomer $t_r$=25.5 min, R isomer $t_r$=28.4 min.

Determination of the absolute configuration of (R)-4-oxo-2-(4-dibenzylamino-2 phenyl)-butyric acid methyl ester by correlation to (S)-2-phenyl-butan-1,4,-diol:

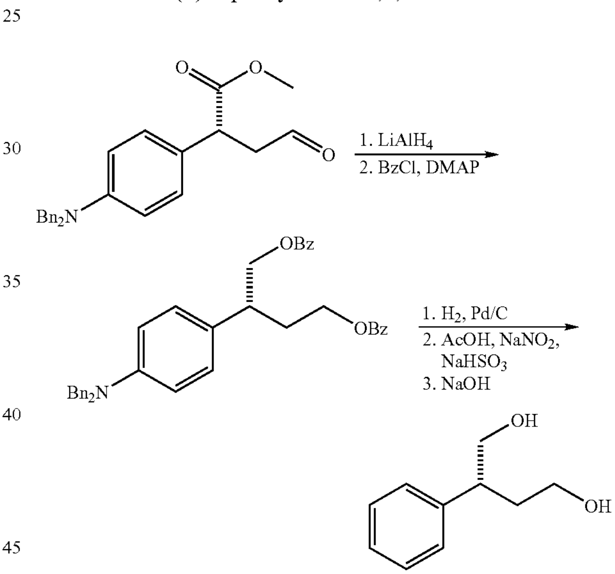

A solution of (R)-4-oxo-2-(4-dibenzylamino-phenyl)-butyric acid methyl ester (848 mg, 2.19 mmol, 1.00 equiv) in $CH_2Cl_2$ (2.5 mL) was added to a stirring suspension of lithium aluminum hydride (332 mg, 8.76 mmol, 4.00 equiv) in $Et_2O$ (15 mL). After 5 min, this mixture was diluted with saturated aqueous sodium potassium tartrate (100 mL) and $Et_2O$ (100 mL) and allowed to stir for an additional 8 h. The organic layer was separated, washed with saturated aqueous NaCl, dried over $Na_2SO_4$, and concentrated in vacuo. This residue was purified via silica gel chromatography (25–100% EtOAc in hexanes) to afford 418 mg of a white solid (1.16 mmol, 53% yield). This substance was exposed to benzoyl chloride (0.777 mL, 6.73 mmol, 2.2 equiv), triethylamine (0.944 mL, 6.73 mmol, 2.2 equiv), DMAP (50 mg) and $CH_2Cl_2$ (15.0 mL) for 24 h at which point the reaction mixture was subjected directly to silica gel chromatography (10–50% EtOAc in hexanes) to afford 556 mg (0.976, 84% yield) of a pale yellow solid assigned as S12. A portion of this material (512 mg, 0.900 mmol, 1.00 equiv) was dissolved in EtOAc (8.0 mL) exposed to a suspension of 10% Pd on carbon (51.3 mg) in MeOH (20 mL) under H atmosphere. After 22 h, the reaction mixture was filtered through Celite and concentrated in vacuo. The resulting residue was purified via silica gel chromatography to afford 323 mg (0.829 mmol, 94% yield) of a pale yellow solid; $[\alpha]_D$=−29.9 (c=1.92, $CHCl_3$). A solution of compound (30.8 mg, 79.1 μmol, 1.00 equiv) in ethanol (4.3 mL) and AcOH (0.64 mL) was treated with $NaNO_2$ (71.0 mg, 1.02 mmol, in 0.64 mL $H_2O$) and $NaHSO_3$ (107 mg, 1.02 mmol, in 0.64 mL $H_2O$). After 3 h, the solution was extracted with $CHCl_3$ and the extracts were collectively washed with $H_2O$ and saturated aqueous NaCl and dried over $Na_2SO_4$. This solution was concentrated in vacuo and the resulting residue was treated with NaOH (100 mg, 2.50 mmol) and methanol (1.0 mL). After one hour, the reaction mixture was partitioned between $CH_2Cl_2$ and $H_2O$, the organic layer was dried over $Na_2SO_4$ and concentrated in vacuo. The residue was subjected to silica gel chromatography (100% EtOAc) followed by concentration in vacuo to afford 4.1 mg (25 μmol, 31% yield from aniline) of a substance that was spectroscopically identical in all respects to the known compound (S)-2-phenyl-butan-1,4,-diol.6 $[\alpha]_D$ (literature)=−13 (c=3.0, $CHCl_3$); $[\alpha]_D$ (observed)=−32.3 (c=0.82, $CHCl_3$).

EXAMPLE 15

(R)-4-Oxo-2-(4-pyrrolidin-1-yl-phenyl)-butyric acid methyl ester (3) (Table 2, entries 4 & 5): To an amber 2-dram vial equipped with a magnetic stir bar was added (2S,5S)-5-benzyl-2-tert-butyl-3-methylimidazolidin-4-one (12.3 mg, 0.0500 mmol, 0.100 equiv), 4-oxobutenoic acid methyl ester (57.1 mg, 0.500 mmol, 1.00 equiv), $CHCl_3$ (0.5 ml), HCl (as a 4N solution in 1,4-dioxane, 12.5 μL, 0.0500 mmol, 0.100 equiv), and 1-phenylpyrrolidine (144 μL, 1.00 mmol, 2.00 equiv). The solution was stirred for 20 min at ambient temperature and subjected directly to silica gel chromatography. Gradient elution with 20–40% EtOAc in hexanes afforded the product as a white powder in 96% yield (126 mg, 0.480 mmol); 95% ee. IR (film) 2974, 2959, 2899, 2827, 2726, 1730, 1718, 1614, 1522, 1488, 1435, 1374, 1229, 1164, 1091, 814, 771, 531 $cm^{-1}$; $^1H$ NMR (300 MHz, $CDCl_3$) δ 9.75 (s, 1H, CHO), 7.12 (d, J=8.8 Hz, 2H, ArH), 6.51 (d, J=8.8 Hz, 2H, ArH), 4.02 (dd, J=4.7, 9.6 Hz, 1H, ArCH), 3.65 (s, 3H, $OCH_3$), 3.33 (dd, J=9.9, 18.4 Hz, 1H, $CH_2CO$), 3.28–3.23 (m, 4H, $N(CH_2)_2$), 2.76 (dd, J=5.0, 18.4 Hz, 1H, $CH_2CO$), 2.01–1.96 (m, 4H, $CH_2(CH_2)_2CH_2$); $^{13}C$ NMR (75 MHz, $CDCl_3$) δ 200.5, 174.2, 147.6, 128.7, 124.1, 112.1, 52.5, 47.8, 47.7, 44.2, 25.7. HRMS (CI) exact mass calcd for ($C_{15}H_{19}NO_3$) requires m/z 261.1443, found m/z 262.1439. $[\alpha]_D$=−147.8 (c=1.0, $CHCl_3$).

The enantiomeric ratio of the product was determined by HPLC analysis of the corresponding alcohol (obtained by $NaBH_4$ reduction) using a Chiracel AD and AD guard column (10% ethanol/hexanes, 1 mL/min); S isomer $t_r$=20.9 min, R isomer $t_r$=24.4 min. The same reaction conducted at −20° C. was complete after 8 h and purified in identical fashion to give the product as a white powder in 97% yield (127 mg, 0.487 mmol); 97% ee. On a 50-mmol scale using 2 mol % amine and 2 mol % HCl at ambient temperature, the reaction afforded the product in 93% yield (12.21 g, 46.7 mmol); 91% ee. A recrystallization of this product from ethyl acetate provided 10.56 g (86% yield) of material in 96% ee.

Determination of the absolute configuration of(R)-4-oxo-2-(4-pyrrolidin-1-ylphenyl)-butyric acid methyl ester by correlation to (S)-2-phenyl-butan-1,4,-diol bis-tertbutyldimethylsilyl ether.

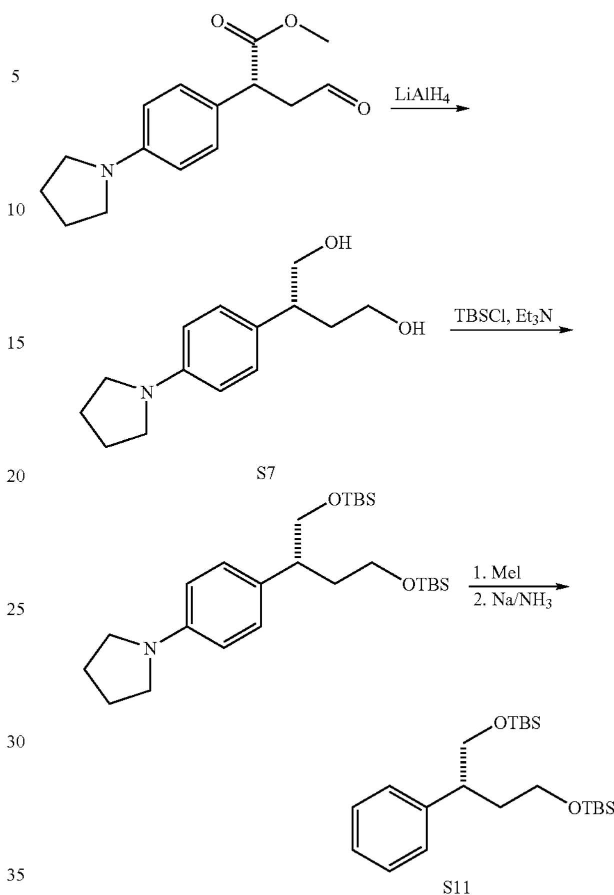

A solution of (R)-4-oxo-2-(4-pyrrolidin-1-yl-phenyl)-butyric acid methyl ester (2.23 g, 8.53 mmol, 1.00 equiv) in THF (15 mL) was added carefully to a stirring suspension of lithium aluminum hydride (1.27 g, 33.5 mmol, 4.0 equiv) in $Et_2O$ (45 mL). After 5 min, this mixture was diluted with saturated aqueous sodium potassium tartrate (100 mL) and $Et_2O$ (100 mL) and allowed to stir for an additional 8 h. The organic layer was separated and the aqueous was extracted three times with $CH_2Cl_2$. The combined organics were washed with saturated aqueous NaCl, dried over $Na_2SO_4$, and concentrated in vacuo. The resulting residue was purified by silica gel chromatography (100% EtOAc) to afford 1.97 g (8.37 mmol, 98% yield) of a white solid assigned as S17; $[\alpha]_D$=−19.1 (c=1.03, $CHCl_3$). This compound was then exposed to tert-butyldimethylsilyl chloride (2.83 g, 18.8 mmol, 2.20 equiv), triethylamine (2.63 mL, 18.8 mmol, 2.2 equiv), and $CH_2Cl_2$ (20 mL). After 7.5 h, the reaction mixture was subjected directly to silica gel chromatography. Gradient elution with 10–20% EtOAc in hexanes followed by concentration in vacuo afforded 3.41 g (7.37 mmol, 86% yield) of a faint-yellow oil. A portion of this substance (1.17 g, 2.53 mmol, 1.00 equiv) was dissolved in $CH_3I$ (0.47 mL, 7.6 mmol, 3.0 equiv) and stirred for 48 h and subsequently diluted with $Et_2O$ and filtered to provide 1.484 g of a yellow solid. A portion of the ammonium salt (128 mg, 0.200 mmol, 1.00 equiv) was suspended in THF (20 mL) and added to a stirring solution of dissolved sodium (18.4 mg, 0.800 mmol, 4.00 equiv) in freshly condensed liquid ammonia (25 ml) at −78° C. After 30 min, the reaction mixture was quenched with excess methanol, diluted with ether (20 mL) and allowed to warm to ambient temperature. The ethereal solution was washed with aqueous HCl (1N) and saturated NaCl and subsequently dried over $Na_2SO_4$. This residue was purified by silica gel chromatography to afford 52.0 mg of S11 (0.132 mmol, 61% yield) that was spectroscopically identical in all respects to the S11 generated above from (R)-4-oxo-2-(4- dimethylamino-phenyl)-butyric acid methyl ester. $[\alpha]_D$ (reference)=−22.0 (c=1.08, $CHCl_3$); $[\alpha]_D$ (observed)=−22.8 (c=0.92, $CHCl_3$).

EXAMPLE 16

(R)-4-Oxo-2-(6-pyrrolidin-1-yl-biphenyl-3-yl)-butyric acid methyl ester (Table 2, entry 6): To an amber 2-dram vial equipped with a magnetic stir bar was added (2S,5S)-5-benzyl-2-tert-butyl-3-methylimidazolidin-4-one (12.3 mg, 0.0500 mmol, 0.100 equiv), 4-oxobutenoic acid methyl ester (57.1 mg, 0.500 mmol, 1.00 equiv), $CHCl_3$ (0.500 ml), HCl (as a 4N solution in 1,4-dioxane, 12.5 μL, 0.0500 mmol, 0.100 equiv), and 2-(pyrrolidin-1-yl)-biphenyl (223 mg, 1.00 mmol, 2.00 equiv). The solution was stirred for 12 h at ambient temperature and subjected directly to silica gel chromatography. Gradient elution with 10–40% EtOAc in hexanes afforded the product as a white powder in 94% yield (158.4 mg, 0.469 mmol); 99% ee. IR (film) 2949, 2871, 2820, 2721, 1734, 1719, 1606, 1505, 1482, 1354, 1329, 1229, 1164, 769.9, 701.1 $cm^{-1}$; $^1H$ NMR (300 MHz, $CDCl_3$) δ 9.78 (s, 1H, CHO), 7.44–7.24 (m, 5H, ArH), 7.13 (dd, J=2.5, 8.5 Hz, 1H, ArH), 7.05 (d, J=2.2 Hz, 1H, ArH), 6.82 (d, J=8.2 Hz, 1H, ArH), 4.07 (dd, J=4.7, 9.9 Hz, 1H, ArCH), 3.67 (s, 3H, $OCH_3$), 3.38 (dd, J=9.9, 18.4 Hz, 1H, $CH_2CO$), 2.94 (m, 4H, $N(CH_2)_2$), 2.81 (dd, J=4.7, 18.4 Hz, 1H, $CH_2CO$), 1.79–1.72 (m, 4H, $CH_2(CH_2)_2CH_2$); $^{13}C$ NMR (75 MHz, $CDCl_3$) δ 200.1, 173.9, 147.5, 142.9, 131.8, 130.3, 129.3, 128.1, 127.1, 126.7, 126.5, 114.9, 52.7, 51.3, 47.8, 44.3, 25.8. HRMS (CI) exact mass calcd for $(C_{21}H_{23}NO_3)$ requires m/z 337.1679, found m/z 337.1678. $[\alpha]_D$=−110.1 (c=1.0, $CHCl_3$). The enantiomeric ratio of the product was determined by HPLC analysis of the corresponding alcohol (obtained by $NaBH_4$ reduction) using a Chiracel AD and AD guard column (10% ethanol/hexanes, 1 mL/min); S isomer $t_r$=13.9 min, R isomer $t_r$=16.5 min.

EXAMPLE 17

(R)-2-(1-Methyl-2,3-dihydro-1H-indol-5-yl)-4-oxobutyric acid methyl ester (Table 2, entries 7 & 8): To a 2-dram vial equipped with a magnetic stir bar was added (2S, 5S)-5-benzyl-2-tert-butyl-3-methylimidazolidin-4-one (12.3 mg, 0.050 mmol, 0.100 equiv), 4-oxobutenoic acid methyl ester (57.1 mg, 0.500 mmol, 1.00 equiv), $CHCl_3$ (0.500 ml), and HCl (as a 4N solution in 1,4-dioxane, 12.5 μL, 0.050 mmol, 0.100 equiv). The reaction vessel was cooled to −20° C. before the addition of 1-methylindoline (133 μL, 1.00 mmol, 2.00 equiv). The solution was stirred for 8 h at −20° C. and then subjected directly to silica gel chromatography. Gradient elution with 20–40% EtOAc in hexanes afforded the product as a colorless oil in 94% yield (116.6 mg, 0.471 mmol); 98% ee. IR (film) 2952, 2923, 2847, 2812, 2728, 1732, 1616, 1499, 1436, 1381, 1276, 1232, 1170, 1086, 1045, 988.7, 815.8, 585.2. $cm^{-1}$; $^1H$ NMR (300 MHz, $CDCl_3$) δ 9.76 (s, 1H, CHO), 6.97 (s, 1H, ArH), 6.94 (d, J=8.0 Hz, 1H, ArH), 6.39 (d, J=8.0 Hz, 1H, ArH), 4.00 (dd, J=4.7, 9.7 Hz, 1H, ArCH), 3.66 (s, 3H, $OCH_3$), 3.32 (ddd, J=0.8, 9.9, 15.7 Hz, 1H, $CH_2CO$), 3.29 (t, J=8.2 Hz, 2H, $NCH_2$), 2.91 (t, J=8.2 Hz, 2H, $ArCH_2$), 2.75 (ddd, J=0.6, 4.9, 18.3 Hz, 1H, $CH_2CO$), 2.73 (s, 3H, $NCH_3$); $^{13}C$ NMR (75 MHz, $CDCl_3$) δ 200.4, 174.2, 153.2, 131.4, 127.1, 126.7, 123.8, 107.3, 56.3, 52.6, 47.9, 44.5, 36.3, 28.8. HRMS (CI) exact mass calcd for $(C_{14}H_{17}NO_3)$ requires m/z 248.1286 for [M+H]+, found m/z 248.1282. $[\alpha]_D$=−128.9 (c=1.0, $CHCl_3$). The enantiomeric ratio of the product was determined by HPLC analysis of the corresponding alcohol (obtained by $NaBH_4$ reduction in ethanol at 0° C.) using a Chiracel AD and AD guard column (10% ethanol/hexanes, 1 mL/min); S isomer $t_r$=13.9 min, R isomer $t_r$=16.5 min. The same reaction conducted on 0.25-mmol scale at ambient temperature over 20 min and purified in identical fashion afforded the product in 93% yield (57.5 mg, 0.233 mmol) and 93% ee.

EXAMPLE 18

(R)-2-(4-Dimethylaminonaphthalen-1-yl)-4-oxobutyric acid methyl ester (Table 2, entry 9): To an amber 2-dram vial under an argon atmosphere and equipped with a magnetic stir bar was added (2S,5S)-5-benzyl-2-tert-butyl-3-methylimidazolidin-4-one (6.1 mg, 0.025 mmol, 0.10 equiv), 4-oxobuteneoic acid methyl ester (28.5 mg, 0.250 mmol, 1.00 equiv), $CHCl_3$ (0.25 ml), HCl (as a 4N solution in 1,4-dioxane, 6.2 μL, 0.025 mmol, 0.10 equiv), and N,N-dimethyl-1-naphthylamine (82.0 μL, 0.500 mmol, 2.00 equiv). The solution was stirred for 36 h at ambient temperature and subjected directly to silica gel chromatography. Gradient elution with 20–40% EtOAc in hexanes afforded the product as a colorless oil in 89% yield (63.8 mg, 0.224 mmol); 93% ee. IR (film) 2940, 2832, 2783, 2724, 1731, 1582, 1455, 1436, 1391, 1214, 1185, 1087, 1043, 767.9 $cm^{-1}$; $^1H$ NMR (300 MHz, $CDCl_3$) δ 9.84 (s, 1H, CHO), 8.29–8.34 (m, 1H, ArH), 7.99–8.04 (m, 1H, ArH), 748–7.58 (m, 2H, ArH), 7.28 (d, J=8.0 Hz, 1H, ArH), 7.02 (d, J=7.7 Hz, 2H, ArH), 4.91 (dd, J=5.2, 9.9 Hz, 1H, ArCH), 3.68 (s, 3H, $OCH_3$), 3.54 (dd, J=9.9, 18.7 Hz, 1H, $CH_2CO$), 2.89 (s, 6H, $N(CH_3)_2$), 2.86 (dd, J=4.2, 18.6 Hz, 1H, $CH_2CO$); $^{13}C$ NMR (75 MHz, $CDCl_3$) δ 200.0, 174.1, 151.0, 132.3, 129.5, 128.5, 126.7, 125.5, 125.4, 125.3, 123, 113.9, 52.8, 47.4, 45.5, 40.7. HRMS (CI) exact mass calcd for $(C_{17}H_{19}NO_3)$ requires m/z 285.1365, found m/z 285.1365. $[\alpha]_D$=−200.7 (c=1.0, $CHCl_3$).

The enantiomeric ratio of the product was determined by HPLC analysis of the corresponding alcohol (obtained by $NaBH_4$ reduction) using a Chiracel AD and AD guard column (10% ethanol/hexanes, 1 mL/min); S isomer $t_r$=14.9 min, R isomer $t_r$=16.9 min.

EXAMPLE 19

(R)-2-(4-Dimethylamino-2-methylphenyl)-4-oxobutyric acid methyl ester (Table 2, entry 10): To an amber 2-dram vial equipped with a magnetic stir bar was added (2S, 5S)-5-benzyl-2-tert-butyl-3-methylimidazolidin-4-one (24.6 mg, 0.100 mmol, 0.200 equiv), 4-oxobutenoic acid methyl ester (57.1 mg, 0.500 mmol, 1.00 equiv), $CHCl_3$ (0.5 ml), HCl (as a 4N solution in 1,4-dioxane, 25.0 μL, 0.100 mmol, 0.200 equiv), and N,N-dimethyl-m-toluidine (145 μL, 1.00 mmol, 2.00 equiv). The solution was stirred for 10 h at −10° C. temperature and subjected directly to silica gel chromatography. Gradient elution with 20–40% EtOAc in hexanes afforded the product as a colorless oil in 89% yield (112 mg, 0.447 mmol); 84% ee. IR (film) 2949, 2892, 2846, 2797, 2731, 1732, 1723, 1611, 1565, 1513, 1482, 1435, 1354, 1295, 1218, 1169, 1109, 1013, 968.6, 902.1, 840.9, 805.6 $cm^-$; $^1H$ NMR (300 MHz, $CDCl_3$) δ 9.79 (s, 1H, CHO), 7.04 (dd, J=2.4, 7.0 Hz, 1H, ArH), 6.55 (dd, J=2.7, 7.5 Hz, 1H1, ArH), 6.54 (s, 1H, ArH), 4.31 (dd, J=5.4, 9.9 Hz, 1H, ArCH), 3.65 (s, 3H, $OCH_3$), 3.35 (ddd, J=0.8, 9.9, 18.7 Hz, 1H, $CH_2CO$), 2.92 (s, 6H, $N(CH_3)_2$), 2.70 (dd, J=0.6, 4.4, 18.4 Hz, 1H, $CH_2CO$); $^{13}C$ NMR (75 MHz, $CDCl_3$) δ 200.3, 174.3, 149.9, 136.8, 127.7, 124.1, 114.7, 110.9, 52.6, 47.4, 40.8, 40.1, 20.7. HRMS (CI) exact mass calcd for ($C_{14}H_{19}NO_3$) requires m/z 250.1443 for [M+H]+, found m/z 250.1446. $[\alpha]_D$=−129.8 (c=1.14, $CHCl_3$).

The enantiomeric ratio of the product was determined by HPLC analysis of the corresponding alcohol (obtained by $NaBH_4$ reduction) using a Chiracel AD and AD guard column (6.0% ethanol/hexanes, 1 mL/min); S isomer $t_r$=13.8 min, R isomer $t_r$=15.4 min.

Determination of the absolute configuration of (R)-4-oxo-2-(4-dimethylamino-2-methylphenyl)-butyric acid methyl ester by correlation to (R)-o-sec-butyl-toluene:

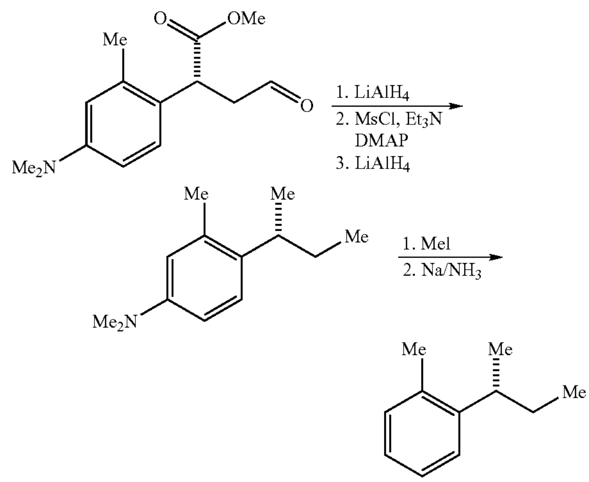

A solution of (R)-4-oxo-2-(4-dimethylamino-2-methylphenyl)-butyric acid methyl ester (499 mg, 2.00 mmol, 1.00 equiv) in $CH_2Cl_2$ (2.0 mL) was added carefully to a stirring suspension of lithium aluminum hydride (304 mg, 8.00 mmol, 4.00 equiv) in $Et_2O$ (50 mL). After 5 min, this mixture was diluted with saturated aqueous sodium potassium tartrate (100 mL) and $Et_2O$ (100 mL) and allowed to stir for an additional 8 h. The organic layer was separated and the aqueous was extracted three times with $CH_2Cl_2$. The combined organics were washed with saturated aqueous NaCl, dried over $Na_2SO_4$, and concentrated in vacuo. The resulting residue was purified by silica gel chromatography to afford 0.224 g (1.00 mmol, 50% yield) of a pale yellow oil. This substance was treated with methanesulfonyl chloride (0.232 mL, 3.00 mmol, 3.00 equiv), triethylamine (0.42 mL, 3.0 mmol, 3.0 equiv), and DMAP (24 mg) in $CH_2Cl_2$ (3 mL). After 2 h, the resulting solution was carefully added to a stirring suspension of lithium aluminum hydride (108 mg, 2.84 mmol, 5.0 equiv) in THF (10 mL) at 0° C. The reaction was allowed to warm to ambient temperature and after 6 h, this mixture was diluted with saturated aqueous sodium potassium tartrate (50 mL) and $Et_2O$ (50 mL) and allowed to stir for an additional 3 h. The organic layer was separated, washed with saturated aqueous NaCl, dried over $Na_2SO_4$, and concentrated in vacuo. The residue was dissolved in an excess of $CH_3I$ (1.0 mL) and stirred for 4 h. The resulting mixture was then concentrated in vacuo and then dissolved in freshly condensed liquid ammonia (50 ml) at −78° C. and treated with sodium (72 mg, 3.0 mmol, 3.0 equiv). Three min later, the reaction mixture was quenched with excess methanol, diluted with ether (50 mL) and allowed to warm to ambient temperature. The resulting residue was purified via silica gel chromatography (1% $Et_2O$ in $CH_2Cl_2$) to afford 16.1 mg of a colorless oil that was spectroscopically identical in all respects to the known compound.7 $[\alpha]_D$ (literature)=+28.6 (c=1.0, $CHCl_3$); $[\alpha]_D$ (observed)=−12.3 (c=0.760, $CHCl_3$), the opposite sign of the rotation indicating that we had produced the enantiomer of the known compound.

EXAMPLE 20

(R)-4-Oxo-2-(4-dimethylamino-2-methoxyphenyl)-butyric acid methyl ester (Table 2, entries 11 & 12): To an amber 2-dram vial equipped with a magnetic stir bar was added (2S, 5S)-5-benzyl-2-tert-butyl-3-methylimidazolidin-4-one (6.13 mg, 0.0250 mmol, 0.100 equiv), 4-methyl ester (28.5 mg, 0.250 mmol, 1.00 equiv), $CHCl_3$ (0.25 ml), HCl (as a 4N solution in 1,4-dioxane, 6.25 μL, 0.0250 mmol, 0.100 equiv), and 3-dimethylamino-anisole (44 μL, 0.30 mmol, 1.2 equiv). The solution was stirred for 5 min at ambient temperature and subjected directly to silica gel chromatography. Gradient elution with 20–40% EtOAc in hexanes afforded the product as a colorless oil in 73% yield (48.2 mg, 0.182 mmol); 91% ee. IR (film) 2950, 2903, 2838, 2727, 1730, 1616, 1569, 1519, 1462, 1440, 1356, 1242, 1171, 1114, 1033, 979.4, 814.6, 642.5 $cm^{-1}$; $^1H$ NMR (300 MHz, $CDCl_3$) δ 9.77 (t, J=1.1 Hz, 1H, CHO), 6.99 (d, J=8.2 Hz, 1H, ArH), 6.27 (dd, J=2.5, 8.5 Hz, 1H, ArH), 6.22 (d, J=2.5 Hz, 1H, ArH) 4.38 (dd, J=5.2, 9.1 Hz, 1H, ArCH), 3.81 (s, 3H, $ArOCH_3$), 3.66 (s, 3H, $CO_2CH_3$), 3.52 (ddd, J=1.4, 9.1, 18.1 Hz, 1H, $CH_2CO$), 2.94 (s, 6H, $N(CH_3)_2$), 2.67 (ddd, J=0.8, 4.9, 17.8 Hz, 1H $CH_2CO$); $^{13}C$ NMR (75 MHz, $CDCl_3$) δ 201.0, 174.4, 157.5, 151.5, 129.3, 114.6, 104.9, 96.2, 55.6, 52.5, 46.7, 40.9, 39.2. HRMS (CI) exact mass calcd for ($C_{21}H_{23}NO_3$) requires m/z 266.1392 for [M+H]+, found m/z 266.1387. $[\alpha]_D$=−149.0 (c=1.0, $CHCl_3$).

The enantiomeric ratio of the product was determined by HPLC analysis of the corresponding alcohol (obtained by $NaBH_4$ reduction in ethanol at 0° C.) using a Chiracel AD and AD guard column (6.0% ethanol/hexanes, 1 mL/min); S isomer $t_r$=26.0 min, R isomer $t_r$=27.8 min. The same reaction conducted at −20° C. on 0.5-mmol scale was complete after 8 h and purified in identical fashion to give the product in 90% yield (119 mg, 0.448 mmol) and 92% ee.

EXAMPLE 21

(R)-4-Oxo-2-(4-dimethylamino-2-methylthio-phenyl)-butyric acid methyl ester (Table 2, entry 13): To a 2-dram vial equipped with a magnetic stir bar was added (2S,5S)-5-benzyl-2-tert-butyl-3-methylimidazolidin-4-one (24.6 mg, 0.100 mmol, 0.100 equiv), 4-oxobuteneoic acid methyl ester (114.1 mg, 1.00 mmol, 1.00 equiv), $CHCl_3$ (1.00 ml), and HCl (as a 4N solution in 1,4-dioxane, 25.0 μL, 0.100 mmol, 0.100 equiv). The reaction vessel was cooled to −20° C. before the addition of 3-dimethylamino-thioanisole (334 mg, 2.00 mmol, 2.00 equiv). The solution was stirred for 20 h at −20° C. and then subjected directly to silica gel chromatography. Gradient elution with 20–40% EtOAc in hexanes afforded the product as a colorless oil in 92% yield (258.6 mg, 0.920 mmol); 91% ee. IR (film) 2950, 2913, 2845, 2711, 1730, 1600, 1554, 1502, 1437, 1353, 1227, 1170, 958.2 $cm^{-1}$; $^{1}H$ NMR (300 MHz, $CDCl_3$) δ 9.75 (s, 1H, CHO), 7.02 (d, J=8.5 Hz, 1H, ArH), 6.66 (d, J=2.5 Hz, 1H, ArH), 6.53 (dd, J=2.8, 8.8 Hz, 1H, ArH), 4.66 (dd, J=4.4, 9.6 Hz, 1H, ArCH), 3.66 (s, 3H, $OCH_3$), 3.25 (ddd, J=1.1, 9.6, 18.1 Hz, 1H, $CH_2CO$), 2.94 (s, 6H, $N(CH_3)_2$), 2.70 (ddd, J=0.8, 4.7, 18.1 Hz, 1H, $CH_2CO$), 2.47 (s, 3H, $SCH_3$); $^{13}C$ NMR (75 MHz, $CDCl_3$) δ 200.0, 173.8, 150.1, 137.3, 128.0, 124.7, 112.3, 110.8, 52.4, 47.1, 41.0, 40.5, 17.6. HRMS (CI) exact mass calcd for ($C_{14}H_{19}NO_3S$) requires m/z 281.1086, found m/z 281.1086. $[\alpha]_D$=−130.1 (c=1.0, $CHCl_3$).

The enantiomeric ratio of the product was determined by HPLC analysis of the corresponding alcohol (obtained by $NaBH_4$ reduction in ethanol at 0° C.) using a Chiracel AD and AD guard column (10% ethanol/hexanes, 1 mL/min); S isomer $t_r$=15.7 min, R isomer $t_r$=17.4 min.

EXAMPLE 22

(R)-4-Oxo-2-(4-dimethylamino-2-chlorophenyl)-butyric acid methyl ester (Table 2, entries 14 & 15): To a 2-dram vial equipped with a magnetic stir bar was added (2S, 5S)-5-benzyl-2-tert-butyl-3-methylimidazolidin-4-one (24.6 mg, 0.100 mmol, 0.200 equiv), 4-oxobutenoic acid methyl ester (57.1 mg, 0.500 mmol, 1.00 equiv), $CHCl_3$ (0.500 ml), and HCl (as a 4N solution in 1,4-dioxane, 18.8 μL, 0.075 mmol, 0.150 equiv). The reaction vessel was cooled to −20° C. before the addition of 3-chloro-N,N-dimethylaniline (156 mg, 1.00 mmol, 2.00 equiv). The solution was stirred for 80 h at −20° C. and then subjected directly to silica gel chromatography. Gradient elution with 20–40% EtOAc in hexanes afforded the product as a colorless oil in 73% yield (98.7 mg, 0.366 mmol); 93% ee. IR (film) 2950, 2900, 2817, 2726, 1734, 1724, 1610, 1512, 1437, 1357, 1285, 1228, 1173, 129, 962.4, 818.5 $cm^{-1}$; $^{1}H$NMR(300 MHz, $CDCl_3$) δ 9.77 (s, 1H, CHO), 7.06 (d, J=8.8 Hz, 1H, ArH), 6.69 (d, J=2.9 Hz, 1H, ArH), 6.56 (dd, J=2.8, 8.8 Hz, 1H, ArH), 4.53 (dd, J=4.7, 9.3 Hz, 1H, ArCH), 3.69 (s, 3H, $OCH_3$), 3.29 (ddd, J=1.1, 9.6, 18.4 Hz, 1H, $CH_2CO$), 2.93 (s, 6H, $N(CH_3)_2$), 2.74 (ddd, J=0.8, 4.9, 18.4 Hz, 1H, $CH_2CO$); $^{13}C$ NMR (75 MHz, $CDCl_3$) δ 199.9, 173.6, 150.7, 134.4, 129.3, 122.6, 113.2, 111.5, 52.8, 46.7, 41.4, 40.6. HRMS (CI) exact mass calcd for ($C_{13}H_{16}ClNO_3$) requires m/z 269.0819, found m/z 269.0814. $[\alpha]_D$=−156.4 (c=1.0, $CHCl_3$).

The enantiomeric ratio of the product was determined by HPLC analysis of the corresponding alcohol (obtained by $NaBH_4$ reduction in ethanol at 0° C.) using a Chiracel AD and AD guard column (6.0% ethanol/hexanes, 1 mL/min); S isomer $t_r$=23.3 min, R isomer $t_r$=25.2 min. The same reaction conducted on 0.25-mmol scale at ambient temperature over 12 h and purified in identical fashion afforded the product in 66% yield (44.4 mg, 0.165 mmol) and 86% ee.

Determination of the absolute configuration of (R)-4-oxo-2-(4-dimethylamino-2-chlorophenyl)-butyric acid methyl ester by correlation to (S)-2-(4'-dimethylamino-phenyl)-butan-1,4,-diol:

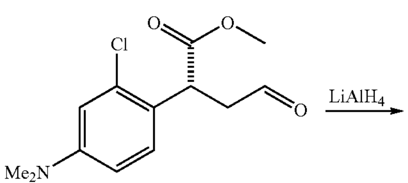

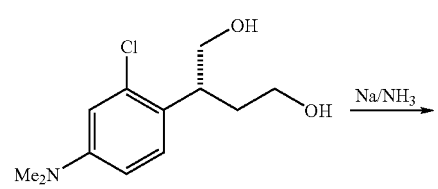

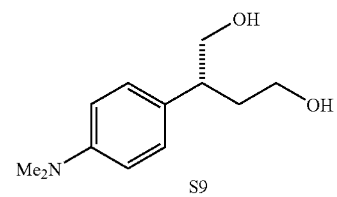

A solution of (R)-4-oxo-2-(4-dimethylamino-2-chlorophenyl)-butyric acid methyl ester (270 mg, 1.00 mmol, 1.00 equiv) in $CH_2Cl_2$ (1.00 mL) was carefully added to a stirring suspension of lithium aluminum hydride (152 mg, 4.00 mmol, 4.00 equiv) in $Et_2O$ (5 mL). After 5 min, this mixture was diluted with saturated aqueous sodium potassium tartrate (100 mL) and $Et_2O$ (100 mL) and allowed to stir for an additional 8 h. The organic layer was separated and the aqueous was extracted three times with $CH_2Cl_2$. The combined organics were washed with saturated aqueous NaCl, dried over $Na_2SO_4$, and concentrated in vacuo. The resulting residue was purified by silica gel chromatography to afford 0.149 g (0.611 mmol, 61% yield) of a white crystalline solid. A portion of this material (21.5 mg, 88.2 pmol, 1.00 equiv) was added to stirring solution of sodium (23 mg, 1.0 mmol, 11 equiv) in liquid ammonia (10 mL) at −50° C. After an hour, the reaction was quenched with methanol and diluted with $Et_2O$ and $H_2O$. The phases were separated and the organic was dried over $Na_2SO_4$ and concentrated in vacuo. The resulting residue was purified via silica gel chromatography (100% EtOAc) to afford 11.1 mg (53.0 μmol, 60% yield) of a white solid that was spectroscopically identical in all respects to S9 generated above from (R)-4-oxo-2-(4-dimethylamino-phenyl)-butyric acid methyl ester. $[\alpha]_D$ (reference)=−23.1 (c=0.975, $CHCl_3$); $[\alpha]_D$ (observed)=−20.5 (c=0.555, $CHCl_3$).

The conditions, yield, and enantioselectivity for the reactions of Examples 13 through 22 are summarized in Table 2:

TABLE 2

Organocatalyzed Alkylation of Methyl 4-Oxobutenoate with Representative Anilines

| entry | $NR_2$ | $R^{12}$ | $R^{13}$ | temp (° C.) | time (h) | % yield | ee |
|---|---|---|---|---|---|---|---|
| 1 | $NMe_2$ | H | H | −10 | 48 | 86 | 96 |
| 2 | $NMe_2$ | H | H | +20 | 5 | 77 | 94 |
| 3 | $NBn_2$ | H | H | +20 | 24 | 65 | 96 |
| 4 | 1-pyrrolidino | H | H | −20 | 8 | 97 | 97 |
| 5 | 1-pyrrolidino | H | H | +20 | 0.3 | 96 | 95 |
| 6 | 1-pyrrolidino | Ph | H | +20 | 12 | 94 | 99 |
| 7 | —N(Me)$CH_2CH_2$— | | H | −20 | 8 | 94 | 98 |
| 8 | —N(Me)$CH_2CH_2$— | | H | +20 | 0.3 | 93 | 93 |
| 9 | $NMe_2$ | —CH═CH—CH═CH— | | +20 | 36 | 89 | 93 |
| 10 | $NMe_2$ | H | Me | −10 | 10 | 89 | 84 |
| 11 | $NMe_2$ | H | OMe | −20 | 8 | 90 | 92 |
| 12 | $NMe_2$ | H | OMe | +20 | 0.1 | 73 | 91 |
| 13 | $NMe_2$ | H | SMe | −20 | 8 | 92 | 91 |
| 14 | $NMe_2$ | H | Cl | −20 | 80 | 73 | 93 |
| 15 | $NMe_2$ | H | Cl | +20 | 12 | 66 | 86 |

As indicated in Table 2, the method of the invention is able to accomodate significant structural variation in the aromatic nucleophile, i.e., the substitued anilines employed as reactants. For example, the reaction was found to proceed efficiently and without loss of enantiocontrol with various nitrogen substituents (entries 1–8, $NMe_2$, $NBn_2$, 1-pyrrolidino, indoline, 93–99% ee) and ring substituents, whether at the ortho or meta positions (entries 6–13, $R_1$ or $R_2$=Ph, Me, OMe, SMe, 84–99% ee). This was also true with respect to an extended ring system (entry 9, 93% ee) and an aniline substituted with an electron-withdrawing substituent (entry 14, 73% yield, 93% ee). Such halogenated benzene adducts can serve as valuable synthons for use in conjuction with organmetallic technologies, e.g., using Still and Suzuki coupling reactions (see Littke et al. (1999), *Agnew. Chem., Int. Ed. Engl.* 38:2411, and Littke et al. (1998), *Agnew. Chem., Int. Ed. Engl.* 37:3387, respectively). Additionally, it should be noted that reactions conducted at room temperature proceeded to completion with operationally convenient reaction times without significant loss in enantioselectivity (e.g., entries 1 and 2, −10° C., 96% ee, 48 h; 20° C., 94% ee, 5 h).

EXAMPLE 23

The effect of catalyst loading on reaction efficiency was evaluated by repeating the reaction of Example 15, at 20° C., at various catalyst loading levels. The results are tabulated in Table 3:

TABLE 3

Effect of Catalyst Loading on Organocatalyzed Alkylations

| entry | mol % catalyst 1 | time | % yield | % ee |
|---|---|---|---|---|
| 1 | 10 | 20 min | 96 | 95 |
| 2 | 5 | 2 h | 92 | 94 |
| 3 | 2 | 12 h | 92 | 92 |
| 4 | 1 | 40 h | 87 | 88 |

While 10 mol % of imidazolidinone 1 resulted in the highest yield and enantioselectivity level, the data in Table 3 indicate that catalyst loadings as low as 1 mol % provided useful levels of enantioselectivity (10 mol % 1, 95% ee; 1, 88% ee).

EXAMPLE 24

This example describes an extended synthesis implementing a 1,4-addition reaction of a substituted aniline to an α,β-unsaturated aldehyde, followed by direct deamination of the incorporated aniline ring, shown schematically as follows:

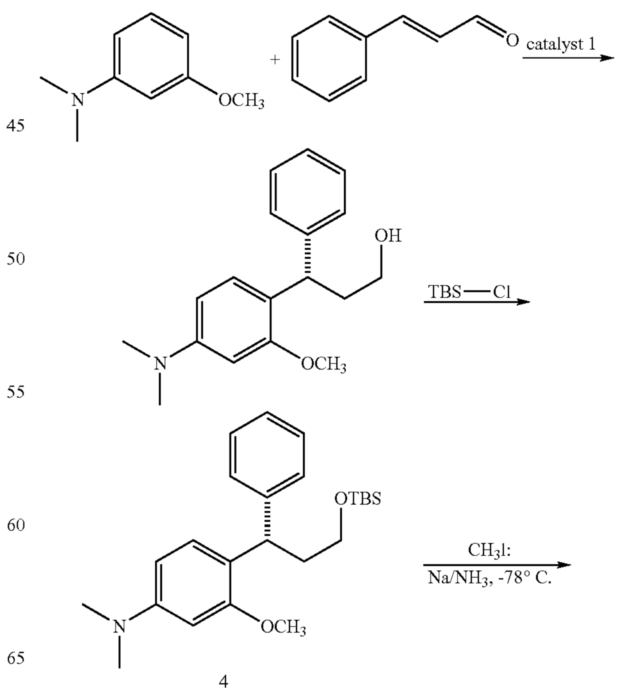

-continued

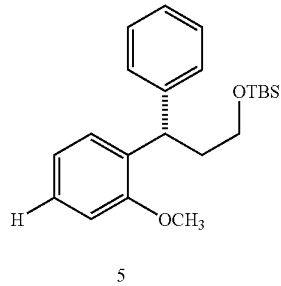

(S)-3-(4-Dimethylamino-2-methoxy-phenyl)-3-phenyl-propanol: To a 50-mL roundbottom flask equipped with a magnetic stir bar was added (2S,5S)-5-benzyl-2-tert-butyl-3-methylimidazolidin-4-one (0.394 g, 1.60 mmol, 0.100 equiv), $CH_2Cl_2$ (16.0 mL), HCl (as a 4N solution in 1,4-dioxane, 0.400 mL, 1.60 mmol, 0.100 equiv), and N,N-dimethyl-m-anisidine (4.69 mL, 32.0 mmol, 2.00 equiv). The reaction vessel was cooled to 0° C. before the addition of cinnamaldehyde (2.06 ml, 16.0 mmol, 1.00 equiv). The solution was stirred for 12 h at 0° C. and then warmed to ambient temperature and stirred for an additional 6 h. At that time, the reaction mixture was added drop-wise to a stirring suspension of $NaBH_4$ (0.750 g, 0.198 mmol, 1.24 equiv) in ethanol. After 5 min, the reduction was quenched with saturated aqueous $NaHCO_3$ solution and diluted with $CH_2Cl_2$. The layers were separated and the organic was washed with saturated aqueous $NaHCO_3$ and brine solutions. The resulting solution was dried over sodium sulfate and concentrated in vacuo to give a pale yellow residue, which was purified by silica gel chromatography. Gradient elution with 25–50% EtOAc in hexanes afforded the product as a colorless oil in 81% yield (3.70 g, 13.0 mmol); 74% ee. $^1$H NMR (300 MHz, $CDCl_3$) δ 7.32–7.12 (m, 5H, ArH), 6.99 (d, J=8.2 Hz, 1H, ArH), 6.31 (dd, J=2.7, 8.8 Hz, 1H, ArH), 6.27 (d, J=2.2, Hz, 1H, ArH), 4.51 (dd, J=6.6, 8.8 Hz, 1H, ArCH), 3.83 (s, 3H, $OCH_3$), 3.65–3.48 (m, 2H, $CH_2OH$), 2.93 (s, 6H, $N(CH_3)_2$), 2.38–2.12 (m, 2H, $CHCH_2$), 1.98 (br s, 1H, OH); $^{13}$C NMR (75 MHz, $CDCl_3$) δ 157.8, 150.5, 145.5, 128.8, 128.4, 128.2, 125.9, 121.3, 105.5, 96.6, 61.6, 55.9, 41.1, 38.7, 38.2.

The enantiomeric ratio of the product was determined by HPLC analysis using a Chiracel AD and AD guard column (10% ethanol/hexanes, 1 mL/min); R isomer $t_r$=12.9 min, S isomer $t_r$=18.1 min.

3-(4-Dimethylamino-2-methoxy-phenyl)-3-phenyl-propanol-tert-butyl-dimethylsilyl ether (4): 3-(4-Dimethylamino-2-methoxy-phenyl)-3-phenyl-propanol (0.250 g, 0.877 mmol, 1.0 equiv) was dissolved in $CH_2Cl_2$ (3.0 mL) and treated sequentially with triethylamine (0.148 mL, 1.05 mmol, 1.20 equiv) and tert-butyldimethylsilyl chloride (0.159 g, 1.05 mmol, 1.20 equiv). The reaction was stirred overnight and then subjected directly to silica gel chromatography. Gradient elution with 10–20% EtOAc in hexanes afforded the product as a pale yellow oil in 75% yield (244 mg, 0.659 mmol). $^1$H NMR (300 MHz, $CDCl_3$) δ 7.35–7.26 (m, 4H, ArH), 7.20–7.13 (m, 2H, ArH), 6.35 (dd, J=2.7, 8.8 Hz, 1H, ArH), 6.29 (d, J=2.4, 1H, ArH), 4.48 (t, J=8.2 Hz. 1H, ArCH), 3.81 (s, 3H, $OCH_3$), 3.63 (t, J=7.1 Hz, 2H, $CH_2O$), 2.97 (s, 6H, $N(CH_3)_2$), 2.33–2.24 (m, 2H, $CHCH_2$), 0.95 (s, 9H, $C(CH_3)3$), 0.06 (s, 6H, $Si(CH_3)_2$); $^{13}$C NMR (75 MHz, $CDCl_3$) δ 158.0, 150.5, 145.8, 128.3, 128.2, 125.7, 122.0, 105.1, 97.0, 62.1, 55.7, 41.2, 39.4, 38.5, 26.4, 18.8, −4.8. $[\alpha]_D$=−15.4 (c=0.82, $CHCl_3$).

Methoxy-2-(3-tert-butyldimethylsiloxy-1-phenyl-propyl)-benzene (5): In a 25-mL pear-shaped flask equipped with a magnetic stir bar, 4a (244 mg, 0.659 mmol, 1.00 equiv) was dissolved in iodomethane (0.41 ml, 6.6 mmol, 10 equiv). The neat reaction mixture was stirred at ambient temperature for 8 h at which time TLC analysis showed the starting material to be completely consumed. The iodomethane was removed in vacuo to furnish the quaternary ammonium iodide quantitatively (335 mg, 0.659 mmol) without need for further purification. $^1$H NMR (300 MHz, $CDCl_3$) δ 7.53–7.52 (d, J=2.7 Hz, 1H, ArH), 7.34 (d, J=8.8, 1H, ArH), 7.28–7.12 (m, 6H, ArH), 4.57 (t, J=7.7 Hz, 1H, ArCH), 4.05 (s, 3H, $OCH_3$), 3.99 (s, 9H, $N(CH_3)3$), 3.55–3.49 (m, 2H, $CH_2O$), 2.20 (q, J=7.7 Hz, 2H, $CHCH_2$), 0.95 (s, 9H, $C(CH_3)3$), 0.06 (s, 6H, $Si(CH_3)_2$); $^{13}$C NMR (75 MHz, $CDCl_3$) δ 158.8, 146.4, 143.0, 137.0, 128.9, 128.6, 128.3, 126.6, 110.0, 103.8, 61.2, 58.5, 58.0, 39.7, 37.6, 26.2, 18.6, −5.0. A portion of the quaternary ammonium salt (100 mg, 0.195 mmol, 1.00 equiv) was dissolved/suspended in tetrahydrofuran (3.0 mL) and added to a rapidly stirring solution of sodium (18.0 mg, 0.782 mmol, 4.0 equiv) in liquid ammonia (approx. 25 mL) at −78° C. After 5 min, the cold reaction mixture was treated with benzylmethyl ether (0.2 mL) and the deep blue color was supplanted almost immediately by a bright orange. The mixture was then treated with isopropanol (2 mL) and stirred at −78° C. for another 5 min by which time all color had dissipated from the reaction. Diethyl ether (20 mL) and saturated aqueous ammonium chloride (10 mL) were added carefully and the reaction vessel was allowed to warm to room temperature. The organic phase was then dried over $Na_2SO_4$, concentrated and the residue purified by silica gel chromatography. Gradient elution with 2–10% EtOAc in hexanes provided the deaminated product in 96% yield (61.2 mg, 0.187 mmol). IR (film) 3027, 2954, 2929, 2856, 1601, 1492, 1462, 1438, 1244, 1100, 1051, 945.9, 834.8, 775.2, 751.9, 698.4 $cm^{-1}$; $^1$H NMR (300 MHz, $CDCl_3$) δ 7.33–7.12 (m, 7H, ArH), 6.93 (dt, J=1.1, 7.7 Hz, 1H, ArH), 6.84 (d, J=8.7 Hz, 1H, ArH), 4.58 (t, J=7.7 Hz, 1H, ArCH), 3.78 (s, 3H, $OCH_3$), 3.58 (t, J=7.1 Hz, 1H, $CH_2O$), 2.27 (dq, J=0.9, 6.6 Hz, 2H, $CHCH_2$), 0.90 (s, 9H, $C(CH_3)3$), 0.00 (s, 6H, $Si(CH_3)_2$); $^{13}$C NMR (75 MHz, $CDCl_3$) δ 157.2, 144.9, 142.0, 133.3, 128.7, 128.5, 128.4, 128.3, 127.9, 127.3, 16.1, 126.0, 61.8, 55.7, 39.8, 38.3, 38.2, 26.3, 18.7, −4.9. HRMS (CI) exact mass calcd for ($C_{22}H_32O_2Si$) requires m/z 357.2250 for [M+H]+, found m/z 357.2244. $[\alpha]_D$=−15.7 (c=0.977, $CHCl_3$).

What is claimed is:

1. A method for carrying out a 1,4-addition reaction between an aromatic nucleophile and an α,β-unsaturated aldehyde, comprising contacting an α,β-unsaturated aldehyde with an aromatic nucleophile having the structure of formula (IV)

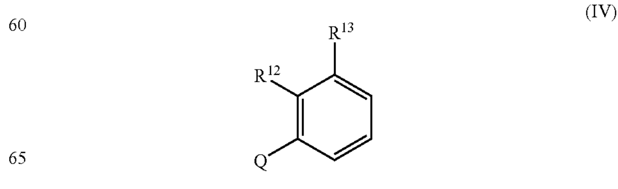

in the presence of a catalyst having the structure of formula (IIA) or (IIB)

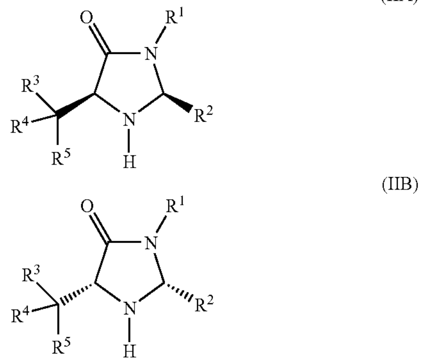

or an acid addition salt thereof, wherein:

$R^1$ is selected from $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl;

$R^2$ has the structure —$(L)_m$—$CR^6R^7R^8$ wherein m is zero or 1, L is $C_1$–$C_6$ alkylene, and $R^6$, $R^7$ and $R^8$ are $C_1$–$C_{12}$ hydrocarbyl;

$R^3$ and $R^4$ are independently selected from hydrogen, halo, hydroxyl, $C_1$–$C_{12}$ hydrocarbyl, substituted $C_1$–$C_{12}$ hydrocarbyl, heteroatom-containing $C_1$–$C_{12}$ hydrocarbyl, and substituted heteroatom-containing $C_1$–$C_{12}$ hydrocarbyl; and $R^5$ is a cyclic group optionally substituted with 1 to 4 non-hydrogen substituents and containing zero to 3 heteroatoms, Q is an electron-donating group; and $R^{12}$ and $R^{13}$ are independently selected from hydrogen, $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, and functional groups, or $R^{12}$ and $R^{13}$, or $R^{12}$ and an atom within Q, taken together, form a cyclic structure selected from five-membered rings, six-membered rings, and fused five-membered and/or six-membered rings, wherein the cyclic structure is aromatic or alicyclic, substituted with zero to 4 non-hydrogen substituents and contains up to 3 heteroatoms per ring.

2. The method of claim 1, wherein:

$R^1$ is $C_1$–$C_{12}$ hydrocarbyl;

$R^3$ and $R^4$ are independently selected from hydrogen and $C_1$–$C_{12}$ hydrocarbyl; and $R^5$ is a monocyclic aryl or heteroaryl group optionally substituted with 1 to 4 substituents selected from halo, hydroxyl, and $C_1$–$C_{12}$ hydrocarbyl.

3. The method of claim 2, wherein:

$R^1$ is $C_1$–$C_6$ alkyl;

m is zero;

$R^6$, $R^7$ and $R^8$ are $C_1$–$C_6$ alkyl;

$R^3$ and $R^4$ are hydrogen; and $R^5$ is phenyl optionally substituted with 1 or 2 substituents selected from halo, hydroxyl, and $C_1$–$C_6$ alkyl.

4. The method of claim 3, wherein:

$R^1$, $R^6$, $R^7$ and $R^8$ are methyl; and $R^5$ is phenyl.

5. The method of claim 3, wherein the catalyst is in the form of an acid addition salt composed of compound (IIA) or (IIB) and a Brønsted acid.

6. The method of claim 5, wherein the catalyst is in the form of an acid addition salt composed of compound (IIA) and a Brønsted acid.

7. The method of claim 1, wherein the α,β-unsaturated aldehyde has the structure of formula (III)

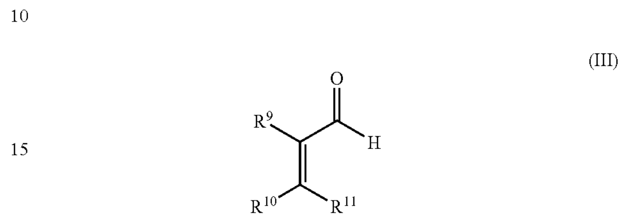

in which $R^9$, $R^{10}$ and $R^{11}$ are independently selected from hydrogen, $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, and functional groups, and further wherein any two of $R^9$, $R^{10}$ and $R^{11}$ taken together form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms.

8. The method of claim 7, wherein $R^9$, $R^{10}$ and $R^{11}$ are independently selected from hydrogen, $C_1$–$C_{24}$ alkyl, $C_2$–$C_{24}$ alkenyl, $C_2$–$C_{24}$ alkynyl, $C_1$–$C_{24}$ alkoxy, $C_2$–$C_{24}$ alkenyloxy, $C_2$–$C_{24}$ alkynyloxy, $C_5$–$C_{30}$ aryl, $C_5$–$C_{30}$ aryloxy, $C_5$–$C_{30}$ haloaryl, $C_5$–$C_{30}$ nitroaryl, $C_2$–$C_{24}$ alkoxyalkyl, $C_6$–$C_{30}$ aryloxyalkyl, hydroxyl, sulfhydryl, $C_2$–$C_{24}$ alkylcarbonyl, $C_6$–$C_{30}$ arylcarbonyl, $C_2$–$C_{24}$ alkoxycarbonyl, $C_6$–$C_{30}$ aryloxycarbonyl, halocarbonyl, $C_2$–$C_{24}$ alkylcarbonato, $C_6$–$C_{30}$ arylcarbonato, carboxy, carboxylato, carbamoyl, mono- and di-($C_1$–$C_{24}$ alkyl)-substituted carbamoyl, mono- and di-($C_5$–$C_{20}$ aryl)-substituted carbamoyl, amino, mono- and di-($C_1$–$C_{24}$ alkyl)-substituted amino, mono- and di-($C_5$–$C_{20}$ aryl)-substituted amino, $C_2$–$C_{24}$ alkylamido, $C_6$–$C_{30}$ arylamido, imino, $C_2$–$C_{24}$ allylimino, $C_6$–$C_{30}$ arylimino, nitro, nitroso, sulfo, sulfonato, $C_1$–$C_{24}$ alkylsulfanyl, $C_5$–$C_{30}$ arylsulfanyl, $C_1$–$C_{24}$ alkylsulfinyl, $C_5$–$C_{30}$ arylsulfinyl, $C_1$–$C_{24}$ alkylsulfonyl, $C_5$–$C_{30}$ arylsulfonyl, phosphono, phosphonato, phosphinato, phospho, phosphino, and combinations thereof.

9. The method of claim 8, wherein $R^9$ and $R^{11}$ are hydrogen.

10. The method of claim 9, wherein $R^{10}$ is selected from hydrogen, $C_1$–$C_{12}$ alkyl, $C_1$–$C_{12}$ alkoxy, $C_5$–$C_{20}$ aryl, $C_2$–$C_{12}$ alkoxyalkyl, $C_2$–$C_{12}$ alkoxycarbonyl, $C_6$–$C_{20}$ aryloxycarbonyl, and $C_6$–$C_{20}$ aryloxyalkyl.

11. The method of claim 10, wherein $R^{10}$ is selected from hydrogen, $C_1$–$C_6$ alkyl, $C_5$–$C_{12}$ aryl, $C_2$–$C_6$ alkoxycarbonyl, $C_6$–$C_{12}$ aryloxycarbonyl, and $C_6$–$C_{12}$ aryloxyalkyl.

12. The method of claim 1, wherein Q is selected from $C_1$–$C_{24}$ alkyl, $C_1$–$C_{24}$ alkoxy, $C_5$–$C_{30}$ aryloxy, $C_6$–$C_{24}$ alkaryl, $C_1$–$C_{24}$ alkylthio, $C_2$–$C_{24}$ alkylcarbonyl, $C_6$–$C_{30}$ arylcarbonyl, $C_2$–$C_{24}$ alkylcarbonyoxyl, $C_6$–$C_{30}$ arylcarbonyloxy, and N,N-disubstituted amino.

13. The method of claim 12, wherein Q is selected from $C_1$–$C_{12}$ alkyl, $C_1$–$C_{12}$ alkoxy, and N,N-disubstituted amino.

14. The method of claim 13, wherein Q is N,N-disubstituted amino, such that the aromatic nucleophile is of the formula (V)

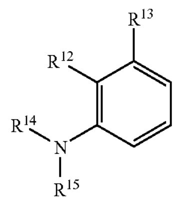

wherein $R^{14}$ and $R^{15}$ are nonhydrogen substituents.

15. The method of claim 14, wherein $R^{14}$ and $R^{15}$ are independently selected from $C_1$–$C_{30}$ hydrocarbyl, heteroatom-containing $C_1$–$C_{30}$ hydrocarbyl, substituted $C_1$–$C_{30}$ hydrocarbyl, substituted heteroatom-containing $C_1$–$C_{30}$ hydrocarbyl, and functional groups, or wherein $R^{14}$ and $R^{15}$, or $R^{14}$ and $R^{12}$, taken together form a cyclic structure selected from five-membered rings, six-membered rings, and fused five-membered and/or six-membered rings, wherein the cyclic structure is aromatic or alicyclic, substituted with zero to 4 non-hydrogen substituents and optionally contains 1 to 3 additional heteroatoms.

16. The method of claim 15, wherein $R^{14}$ and $R^{15}$ are independently selected from $C_1$–$C_{12}$ alkyl, $C_1$–$C_{12}$ heteroalkyl, substituted $C_1$–$C_{12}$ alkyl, substituted $C_1$–$C_{12}$ heteroalkyl, and $C_5$–$C_{12}$ aryl, or together form a five- or six-membered alicyclic group substituted with zero to 2 nonhydrogen substituents and may contain 1 or 2 additional heteroatoms.

17. The method of claim 16, wherein $R^{14}$ and $R^{15}$ are independently selected from $C_1$–$C_6$ alkyl and $C_5$ or $C_6$ aryl, or are taken together to form a linkage resulting in a five- or six-membered alicyclic group.

18. The method of claim 14, wherein $R^{12}$ and $R^{13}$ are independently selected from hydrogen, $C_1$–$C_{24}$ alkyl, $C_1$–$C_{24}$ alkoxy, $C_1$–$C_{24}$ alkylthio, $C_5$–$C_{30}$ aryl, $C_5$–$C_{30}$ aryloxy, $C_5$–$C_{30}$ arylthio, $C_2$–$C_{24}$ alkoxyalkyl, $C_6$–$C_{30}$ aryloxyalkyl, hydroxyl, and sulfhydryl, or are taken together to form a five- or six-membered aromatic ring.

19. The method of claim 18, wherein $R^{12}$ and $R^{13}$ are independently selected from hydrogen, $C_1$–$C_6$ alkyl, $C_1$–$C_6$ alkoxy, and $C_1$–$C_6$ alkylthio, or taken together form an additional benzene ring.

20. The method of claim 14, wherein at least one of $R^{12}$ and $R^{13}$ is an electron-donating substituent.

21. The method of claim 14, wherein $R^{12}$ or $R^{13}$ is an electron-withdrawing substituent.

22. A method for carrying out a 1,4-addition reaction between an aromatic nucleophile and an α,β-unsaturated aldehyde, comprising contacting an α,β-unsaturated aldehyde having the structure $R^{10}$—CH═CH—(CO)—H, wherein $R^{10}$ is selected from hydrogen, $C_1$–$C_6$ alkyl, $C_5$–$C_2$ aryl, $C_2$–$C_6$ alkoxycarbonyl, $C_6$–$C_{12}$ aryloxycarbonyl, and $C_6$–$C_{12}$ aryloxyalkyl, with an aromatic nucleophile having the structure of formula (V)

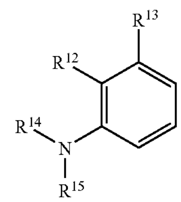

wherein $R^{12}$ and $R^{13}$ are independently selected from hydrogen, $C_1$–$C_6$ alkyl, $C_1$–$C_6$ alkoxy, and $C_1$–$C_6$ alkylthio, or taken together form an additional benzene ring, $R^{14}$ and $R^{15}$ are independently selected from $C_1$–$C_{12}$ alkyl, $C_1$–$C_{12}$ heteroalkyl, substituted $C_1$–$C_{12}$ alkyl, substituted $C_1$–$C_{12}$ heteroalkyl, and $C_5$–$C_{12}$ aryl, or $R^{14}$ and $R^{15}$, or $R^{14}$ and $R^{12}$, taken together form a five- or six-membered alicyclic group that is optionally substituted and/or heteroatom-containing, or $R^{14}$ and $R^{12}$ taken together form a five- or six-membered alicyclic group substituted with zero to 2 nonhydrogen substituents and optionally contains 1 or 2 additional heteroatoms, in the presence of a catalyst composed of an acid addition salt of a Brønsted acid and a compound having the structure of formula (IIA) or (IIB)

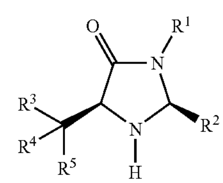

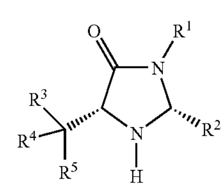

wherein:

$R^1$ is $C_1$–$C_6$ alkyl;

m is zero;

$R^6$, $R^7$ and $R^8$ are $C_1$–$C_6$ alkyl;

$R^3$ and $R^4$ are hydrogen; and $R^5$ is phenyl optionally substituted with 1 or 2 substituents selected from halo, hydroxyl, and $C_1$–$C_6$ alkyl.

23. A method for synthesizing an aldehyde that is substituted at the β position with a benzene ring, comprising carrying out the reaction of claim 14 to provide an aldehyde substituted at the β position with a para(N,N-disubstituted amino) benzene group, quaternizing the N,N-disubstituted amino moiety, and reducing the quaternized para-amino benzene group with sodium in liquid ammonia.

* * * * *